US008574604B2

(12) United States Patent
Esfand et al.

(10) Patent No.: US 8,574,604 B2
(45) Date of Patent: Nov. 5, 2013

(54) METHODS AND COMPOSITIONS FOR THE DELIVERY OF BIOLOGICALLY ACTIVE AGENTS

(75) Inventors: Roseita Esfand, Mississauga (CA); Paul J. Santerre, Whitby (CA); Meilin Yang, Mississauga (CA)

(73) Assignee: Interface Biologics, Inc., Toronto (CA)

( * ) Notice: Subject to any disclaimer, the term of this patent is extended or adjusted under 35 U.S.C. 154(b) by 702 days.

(21) Appl. No.: 11/404,290

(22) Filed: Apr. 14, 2006

(65) Prior Publication Data
US 2007/0037891 A1 Feb. 15, 2007

Related U.S. Application Data

(60) Provisional application No. 60/672,158, filed on Apr. 15, 2005.

(51) Int. Cl.
*A01N 25/00* (2006.01)

(52) U.S. Cl.
USPC .............. 424/405; 424/78.08; 424/78.17; 424/78.18; 424/78.31; 424/78.37

(58) Field of Classification Search
USPC ........................................................ 424/405
See application file for complete search history.

(56) References Cited

U.S. PATENT DOCUMENTS

| | | | |
|---|---|---|---|
| 4,788,176 A | 11/1988 | Wieserman et al. | |
| 4,792,354 A | 12/1988 | Matsuo et al. | |
| 4,810,784 A | 3/1989 | Larm | |
| 4,841,007 A | 6/1989 | Zdrahala et al. | |
| 5,235,003 A | 8/1993 | Ward et al. | |
| 5,322,659 A | 6/1994 | Walder et al. | |
| 5,328,955 A | 7/1994 | Rhee et al. | |
| 5,527,893 A | 6/1996 | Burns et al. | |
| 5,589,563 A | 12/1996 | Ward et al. | |
| 6,127,507 A | 10/2000 | Santerre | |
| 6,316,018 B1 * | 11/2001 | Ding et al. | 424/423 |
| 6,770,725 B2 | 8/2004 | Santerre | |
| 6,858,229 B1 * | 2/2005 | Hubbell et al. | 424/484 |
| 2003/0040790 A1 | 2/2003 | Furst | |
| 2003/0097120 A1 * | 5/2003 | Santerre | 604/891.1 |
| 2004/0063805 A1 | 4/2004 | Pacetti et al. | |

FOREIGN PATENT DOCUMENTS

| | | |
|---|---|---|
| CN | 1083822 | 3/1994 |
| JP | 2004-524891 | 8/2004 |
| WO | WO 93/25212 | 12/1993 |
| WO | WO 95/03036 A1 | 7/1994 |
| WO | WO 01/08718 | 2/2001 |
| WO | WO 01/28524 | 4/2001 |
| WO | WO 02/060350 | 8/2002 |
| WO | WO 02/098477 | 12/2002 |
| WO | WO 2007/004067 A2 | 4/2006 |

OTHER PUBLICATIONS

Ferruti et al., "Recent Results on Functional Polymers and Macromonomers of Interest as Biomaterials or for Biomaterial Modification," *Biomaterials*, 15(15):1235-1241 (1994).
Kumar et al., "Aqueous Polyurethane Dispersions and its Prospects as Nonpolluting Coatings," *Journal of the Colour Society*, 25:19-22 (1985).
Smith et al., "Self-Assembly Using Dendritic Building Blocks—Towards Controllable Nanomaterials," *Progress in Polymer Science*, 30:220-293 (2005).
Tabata et al., "Targeting of Tumor Necrosis Factor to Tumor by use of Dextran and Metal Coordination," *Journal of Controlled Release*, 59:187-196 (1999).
Thünemann et al., "Poly(ethylene oxide)-b-poly-(L-lysine) Complexes with Retinoic Acid," *Macromolecules*, 33:5906-5911 (2000).
International Preliminary Report on Patentability for International Application No. PCT/IB2006/002351, dated Oct. 16, 2007.
International Search Report for International Application No. PCT/IB2006/002351, dated Mar. 27, 2007.
Written Opinion of the International Searching Authority for International Application No. PCT/IB2006/002351, dated Mar. 27, 2007.
Fischell, "Polymer Coatings for Stents: Can We Judge a Stent by Its Cover?" *Circulation* 94:1494-1495 (1996).
Sukenik et al., "Modulation of Cell Adhesion by Modification of Titanium Surfaces with Covalently Attached Self-Assembled Monolayers," *J. Biomed. Mat. Res.* 24:1307-1323 (1990).
Synytska et al., "Perfluoroalkyl End-Functionalized Oligoesters: Correlation between Wettability and End-Group Segregation," *Macromolecules* 40:297-305 (2007).
Ward et al., "In Vivo Biostability of Polyether Polyurethanes With Fluoropolymer and Polyethylene Oxide Surface Modifying Endgroups; Resistance to Metal Ion Oxidation," *J. Biomed. Mater. Res.* 80A: 34-44 (2007).
Ward et al., "In Vivo Biostability of Polyether Polyurethanes With Fluoropolymer Surface Modifying Endgroups: Resistance to Biologic Oxidation and Stress Cracking," *J. Biomed. Mater. Res.* 79A: 827-835 (2006).
Ward et al., "In Vivo Biostability of Shore 55D Polyether Polyurethanes With and Without Fluoropolymer Surface Modifying Endgroups," *J. Biomed. Mater. Res.* 79A: 836-845 (2006).
English language translation of the first examination report mailed in Chinese Patent Application No. 200680021215.5, dated May 27, 2010.
English Translation of Notice of Reasons for Rejection, in Japanese Patent Application No. 2008-505994, mailed Feb. 6, 2013 (4 pages).
Ikeda et al., "Polyurethane elastomer with PEO-PTMO-PEO soft segment for sustained release of drugs," *Biomaterials* 11: 553-560, 1990.
Japanese Language Notice of Reasons for Rejection pertaining to Japanese Patent Application No. 2008-505994, issued Dec. 12, 2011.

* cited by examiner (Continued)

*Primary Examiner* — James Rogers
(74) *Attorney, Agent, or Firm* — Clark & Elbing LLP; Kristina Bieker-Brady

(57) ABSTRACT

The invention features polymers noncovalently complexed with a biologically active agent. The polymer complexes include at least one shielding moiety covalently tethered to at least one complexing moiety, which is complexed with at least one biologically active agent.

24 Claims, 19 Drawing Sheets

Figure 1A:
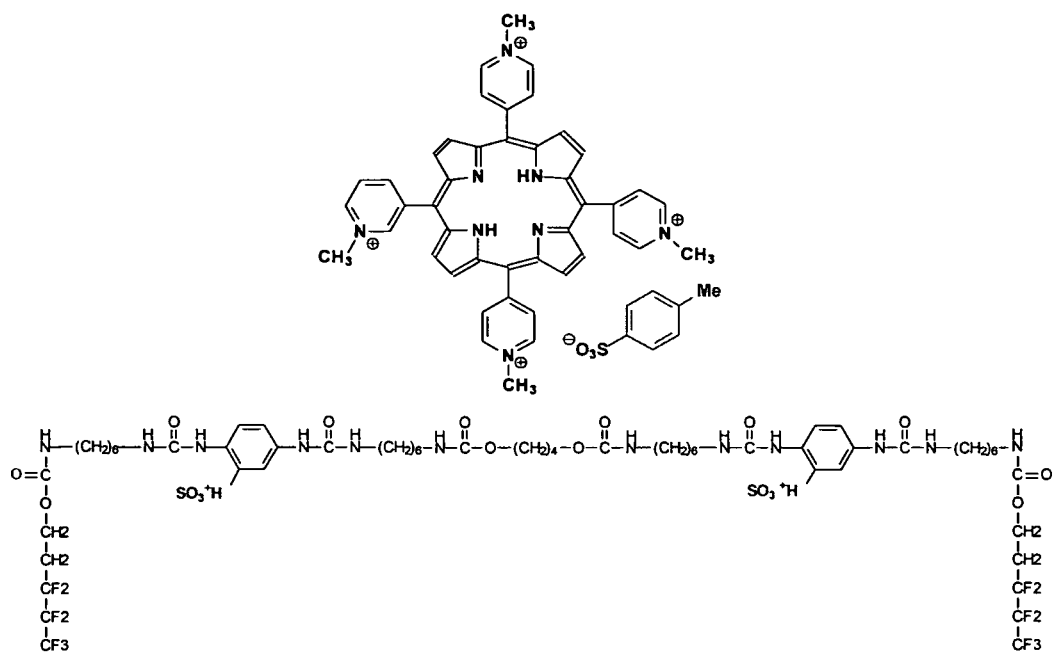
Figure 1B:
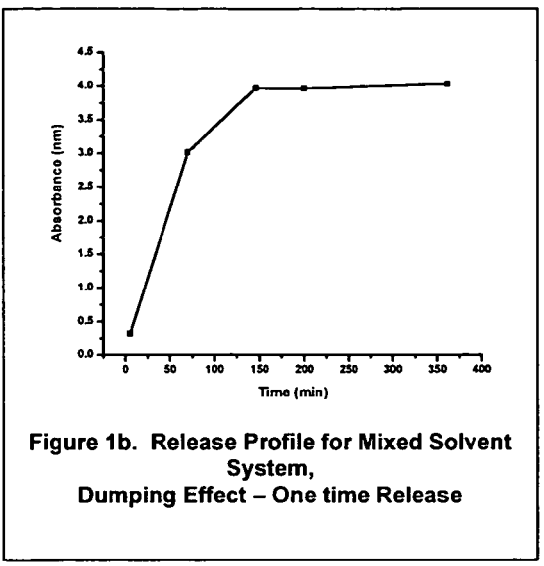

Figure 1b. Release Profile for Mixed Solvent System, Dumping Effect – One time Release Figure 1c. Release Profile (1M-HCl)

Figure 1C:
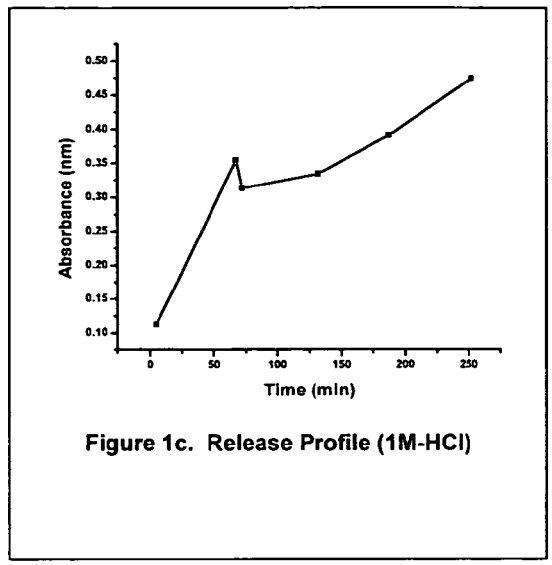
Figure 1D:
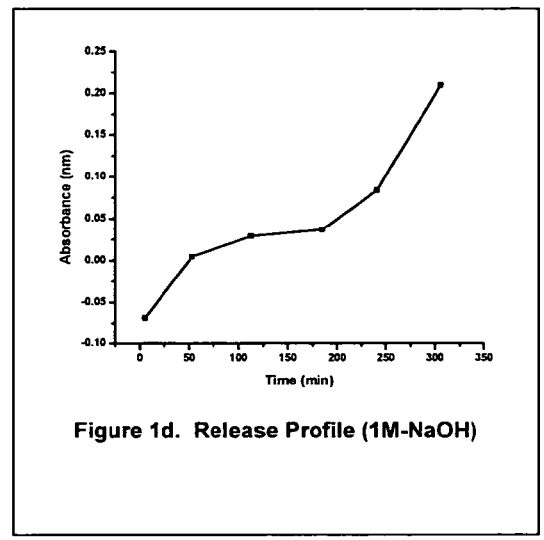

Figure 1d. Release Profile (1M-NaOH)

Figure 1E:
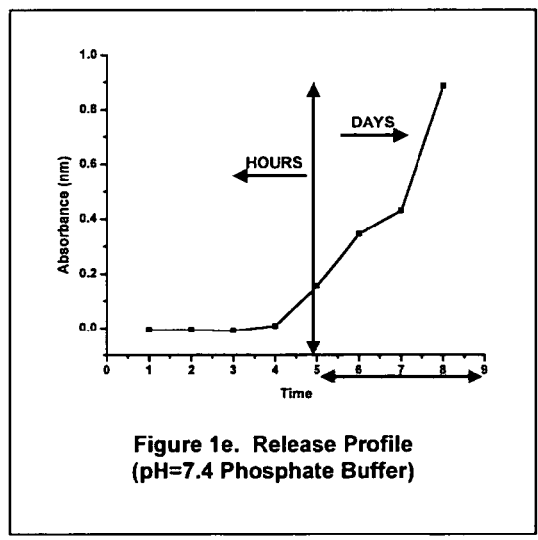

Figure 1e. Release Profile (pH=7.4 Phosphate Buffer)

Figures 2a-2d

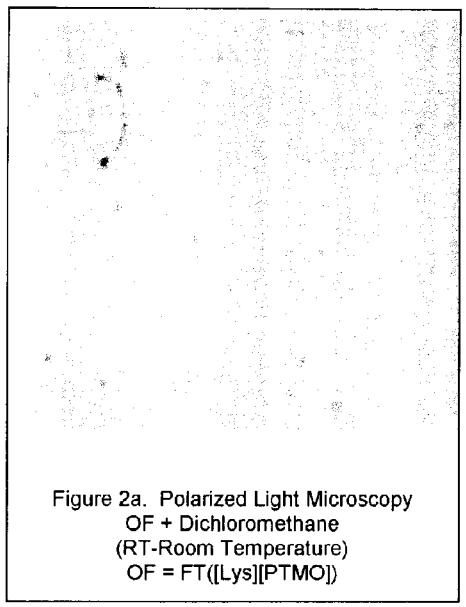

Figure 2a. Polarized Light Microscopy
OF + Dichloromethane
(RT-Room Temperature)
OF = FT([Lys][PTMO])

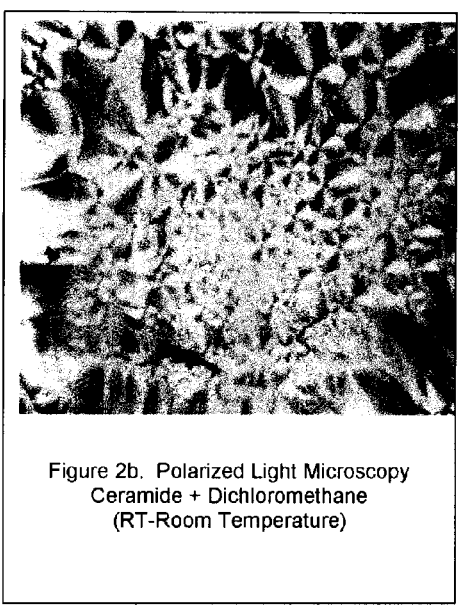

Figure 2b. Polarized Light Microscopy
Ceramide + Dichloromethane
(RT-Room Temperature)

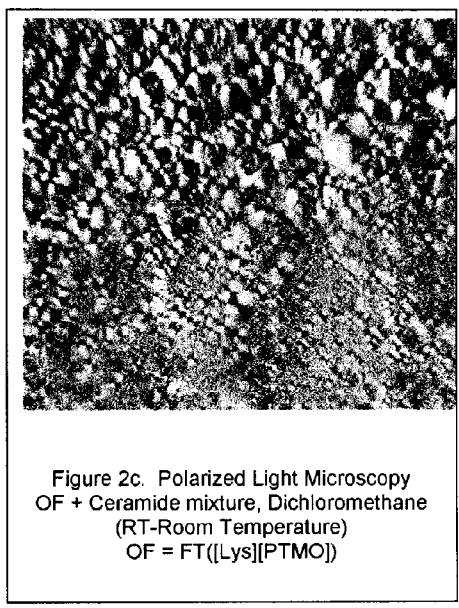

Figure 2c. Polarized Light Microscopy
OF + Ceramide mixture, Dichloromethane
(RT-Room Temperature)
OF = FT([Lys][PTMO])

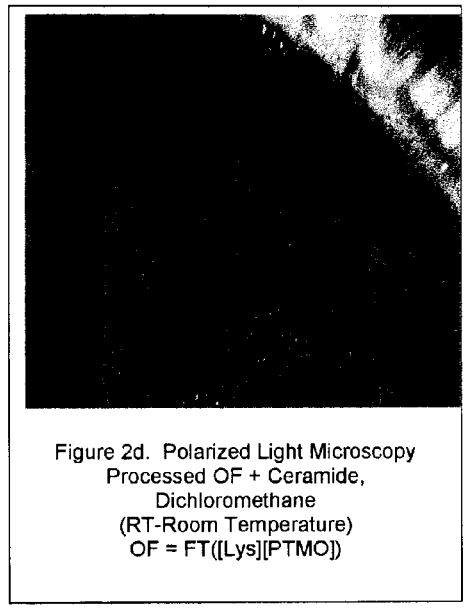

Figure 2d. Polarized Light Microscopy
Processed OF + Ceramide,
Dichloromethane
(RT-Room Temperature)
OF = FT([Lys][PTMO])

Figure 2E:
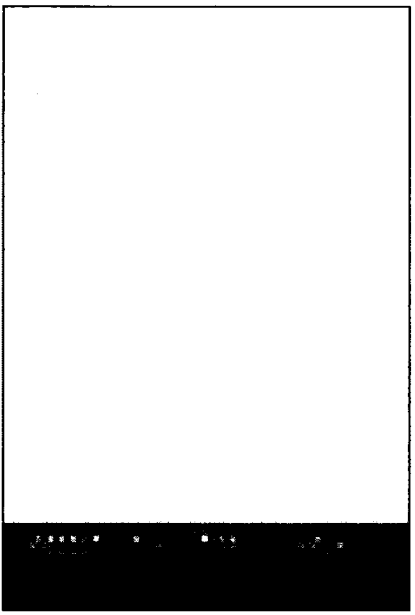

Figure 2e. SEM
OF + Dichloromethane
(RT-Room Temperature)
OF = FT([Lys][PTMO])

Figure 2F:
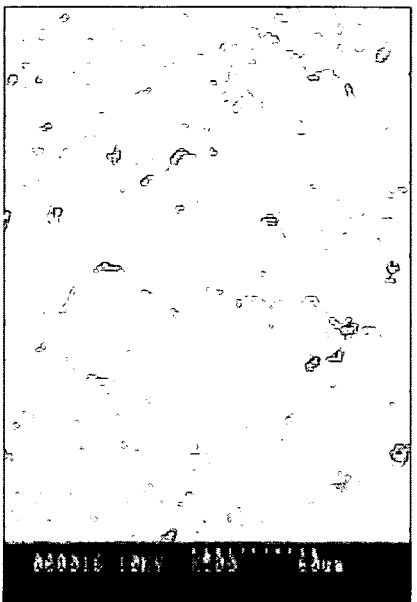

Figure 2f. SEM
Ceramide + Dichloromethane
(RT-Room Temperature)

Figure 2G:
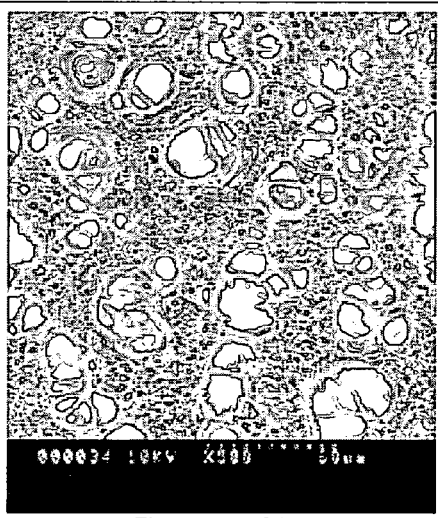

Figure 2g. SEM
OF + Ceramide mixture, Dichloromethane
(RT-Room Temperature)
OF = FT([Lys][PTMO])

Figure 2H:
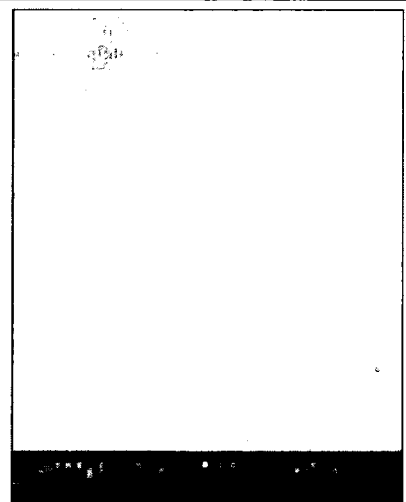

Figure 2h. SEM
Processed OF + Ceramide,
Dichloromethane
(RT-Room Temperature)
OF = FT([Lys][PTMO])

2i. Stainless Steel (304) – Coated with
Processed OF + Ceramide, Dichloromethane
(RT-Room Temperature)
OF = FT([Lys][PTMO])

2j. Stainless Steel (304) – Coated with
Processed OF + Ceramide, Dichloromethane
(RT-Room Temperature)
OF = FT([Lys][PTMO])

Figures 2k and 2l
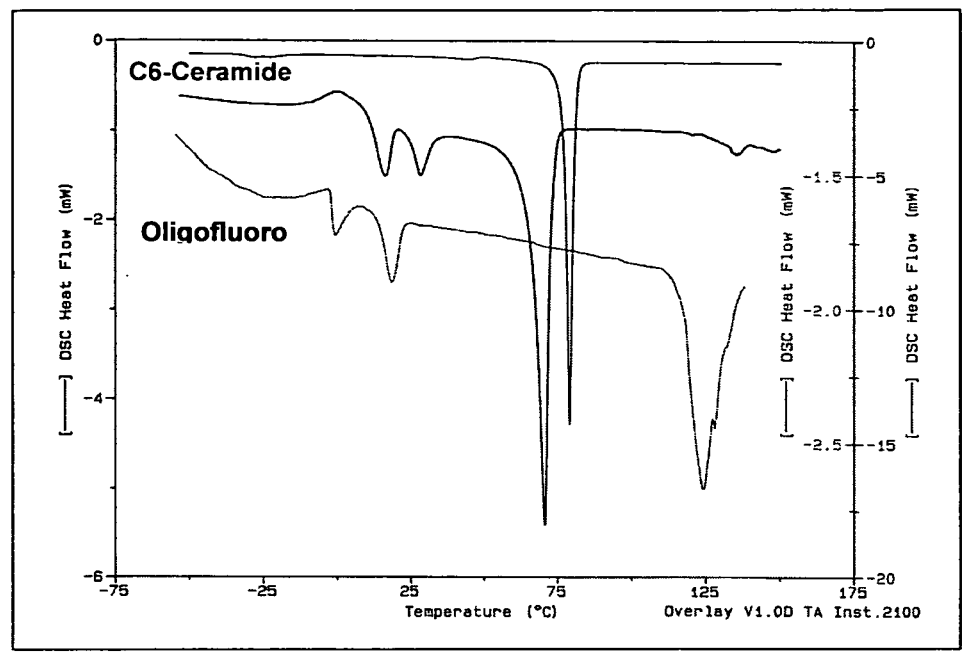
Fig. 2k
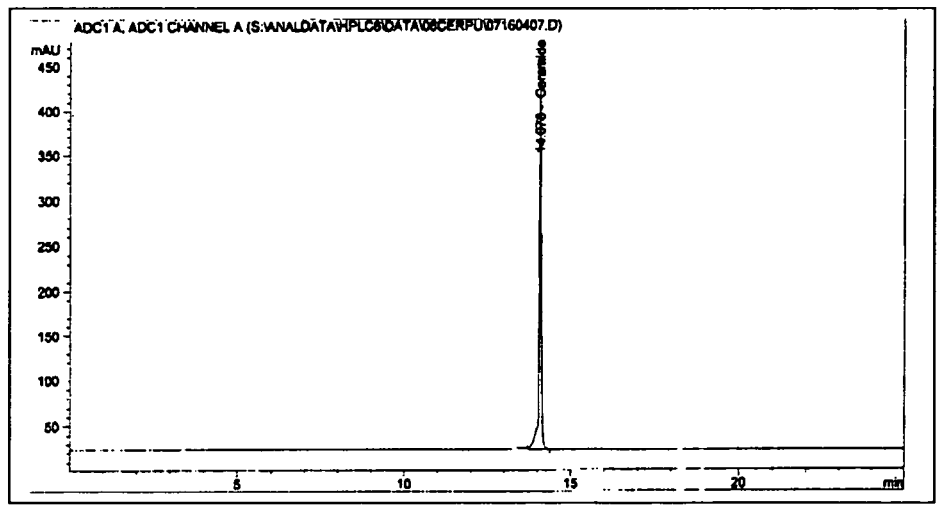
Fig. 2l

Figure 2I:
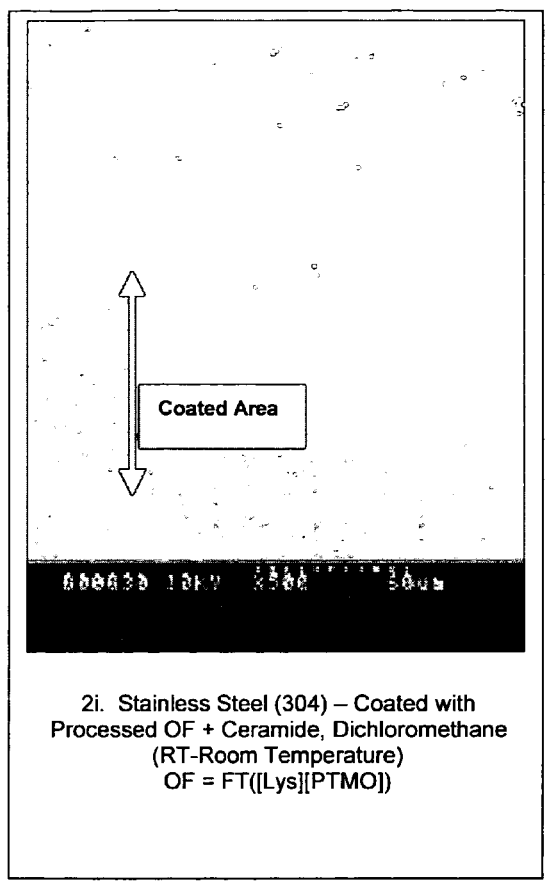
Figure 2J:
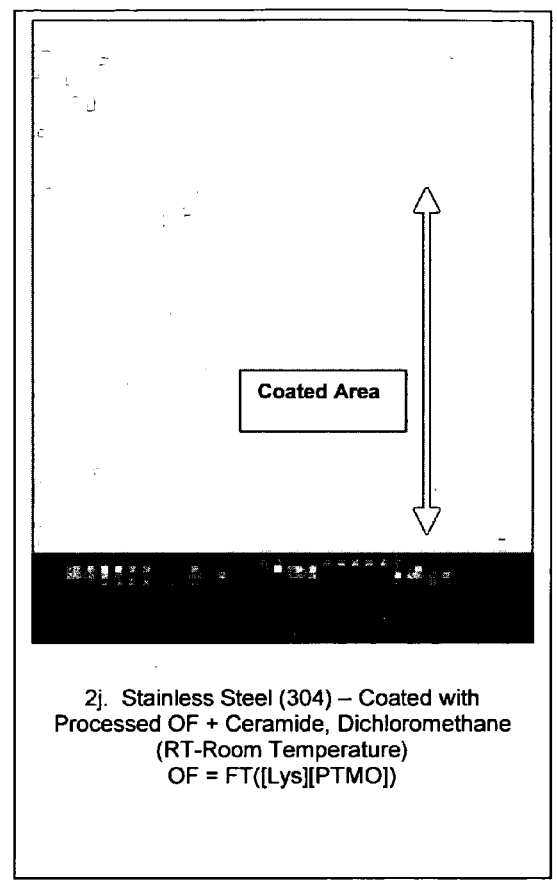
Figure 2M:
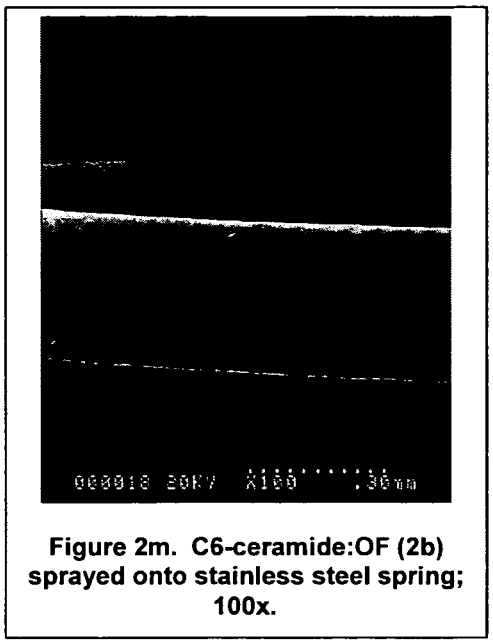

Figure 2m. C6-ceramide:OF (2b) sprayed onto stainless steel spring; 100x.

Figure 2N:
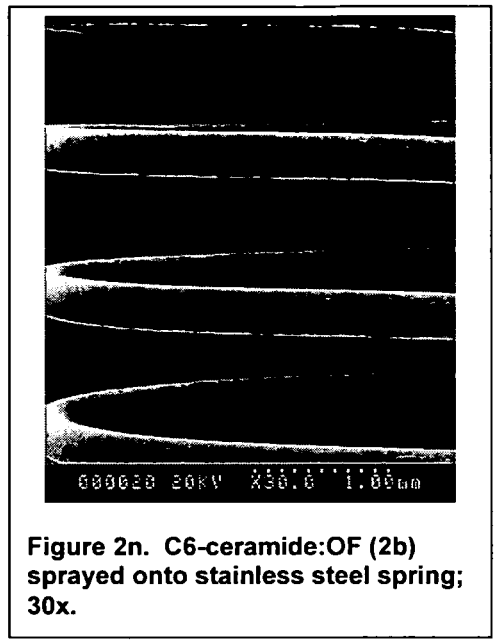

Figure 2n. C6-ceramide:OF (2b) sprayed onto stainless steel spring; 30x.

Figure 2O:
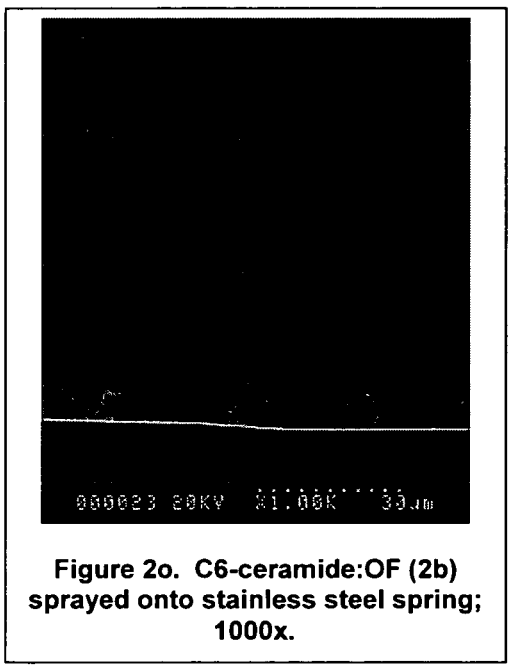

Figure 2o. C6-ceramide:OF (2b) sprayed onto stainless steel spring; 1000x.

Figure 2P:
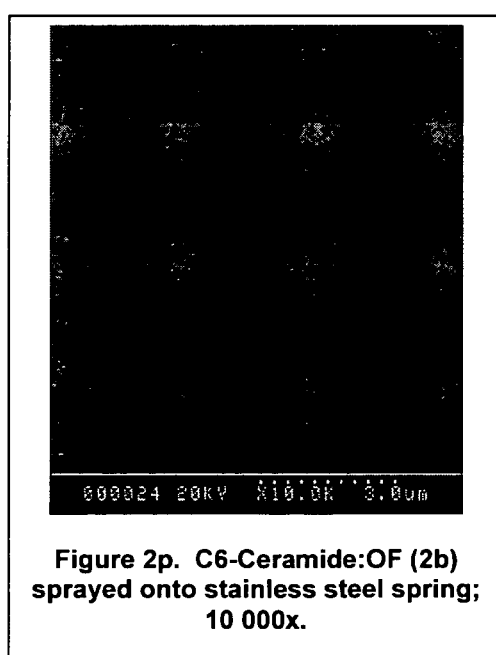
Figure 2Q:
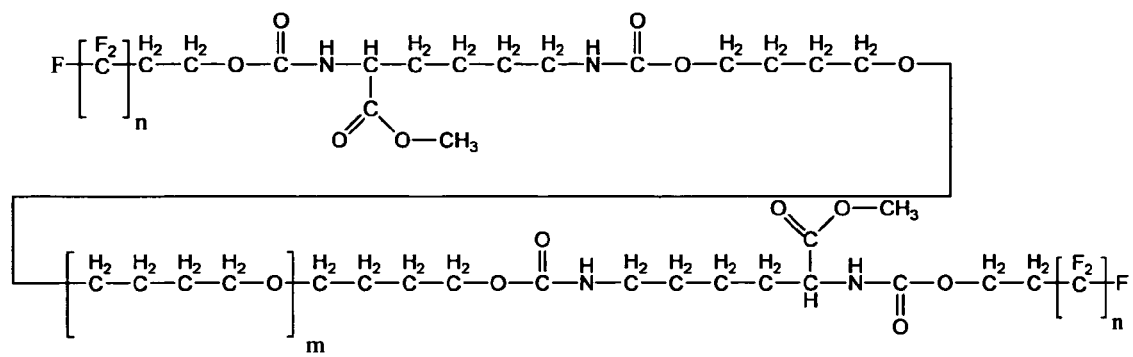

Figure 2p. C6-Ceramide:OF (2b) sprayed onto stainless steel spring; 10 000x.

Figures 3a and 3b
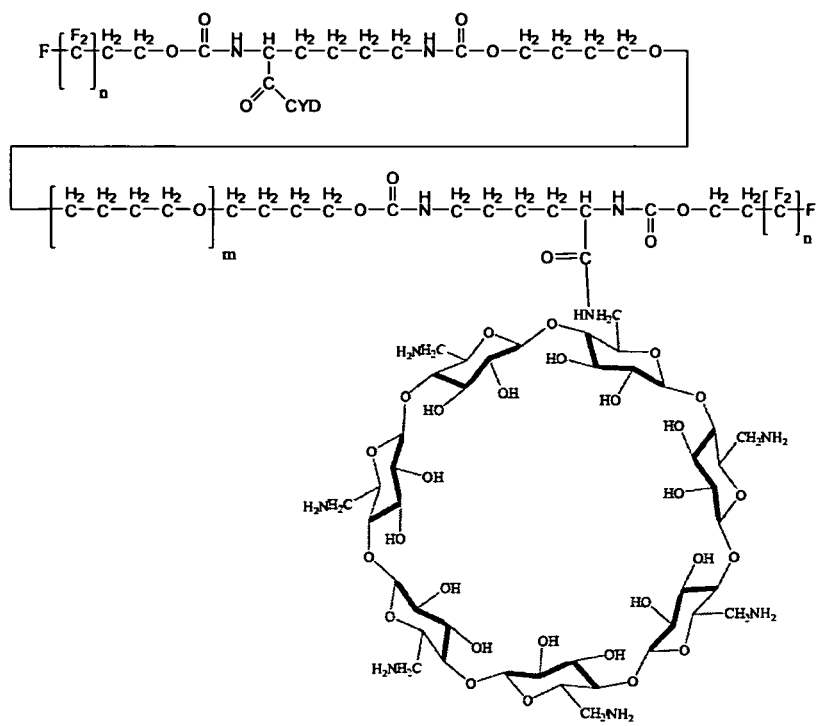
Fig. 3a
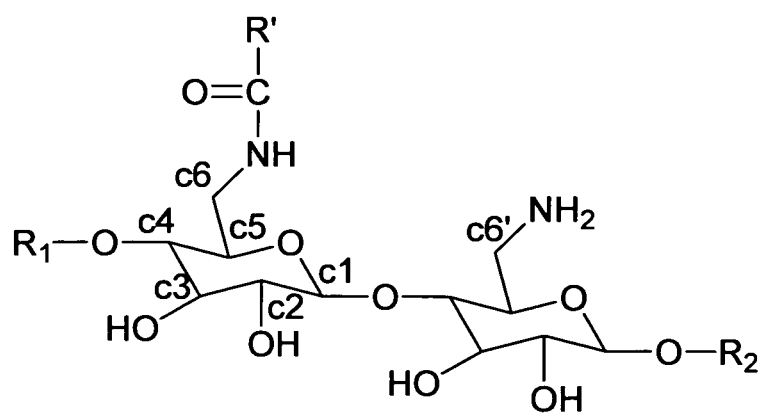
Fig. 3b

Figures 4a and 4b
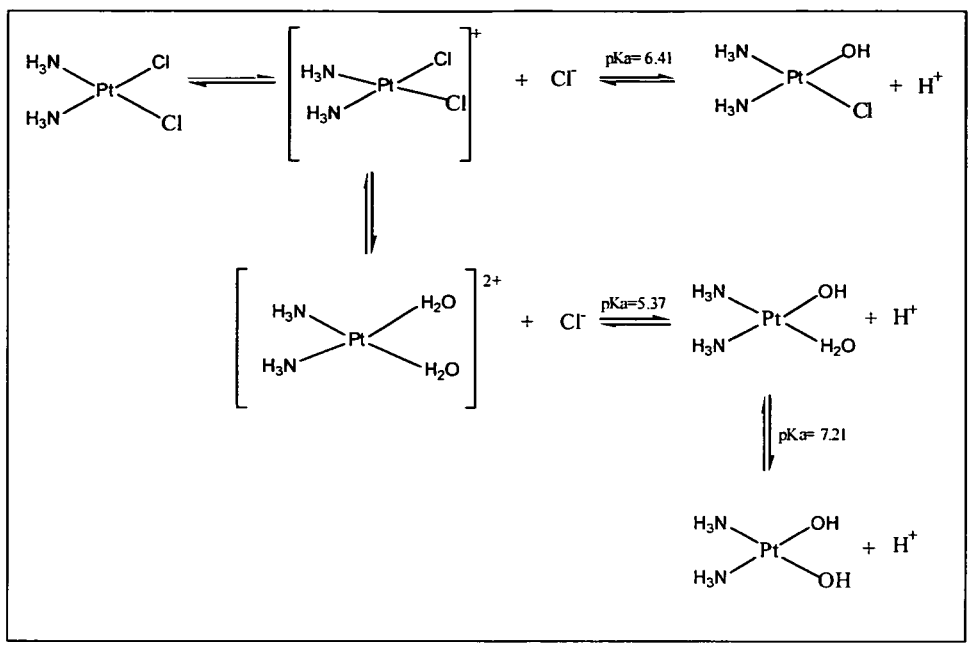
Fig. 4a
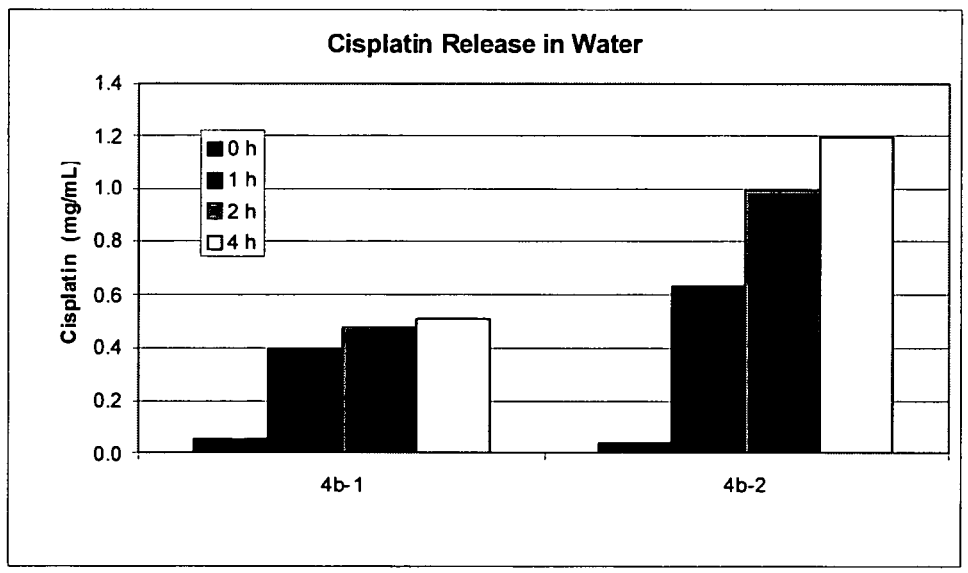
Fig. 4b

Figures 5a and 5d(a)
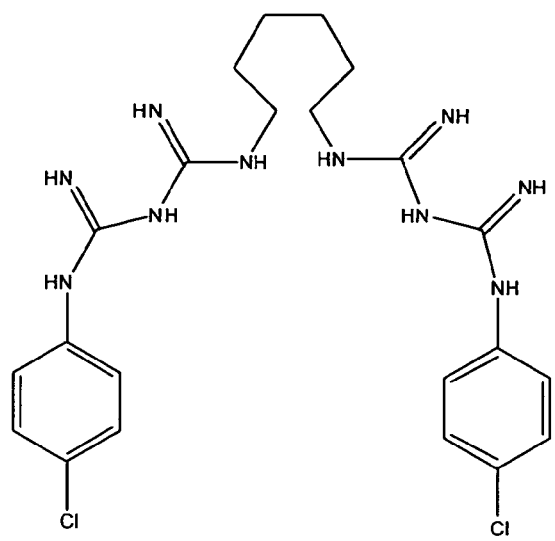
Fig.5A
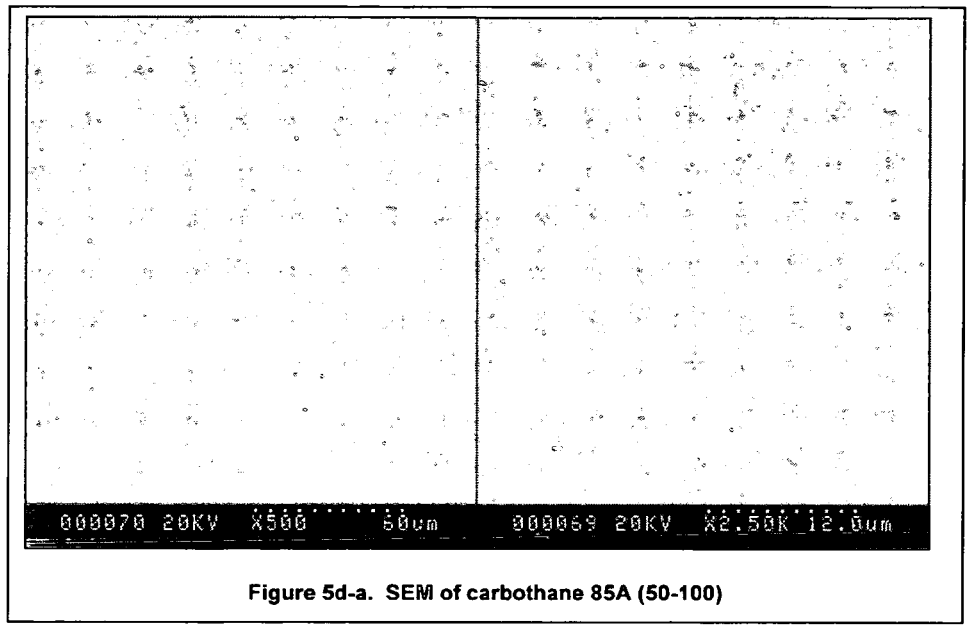
Fig. 5d(a)

Figures 5d(b) and 5d(c)
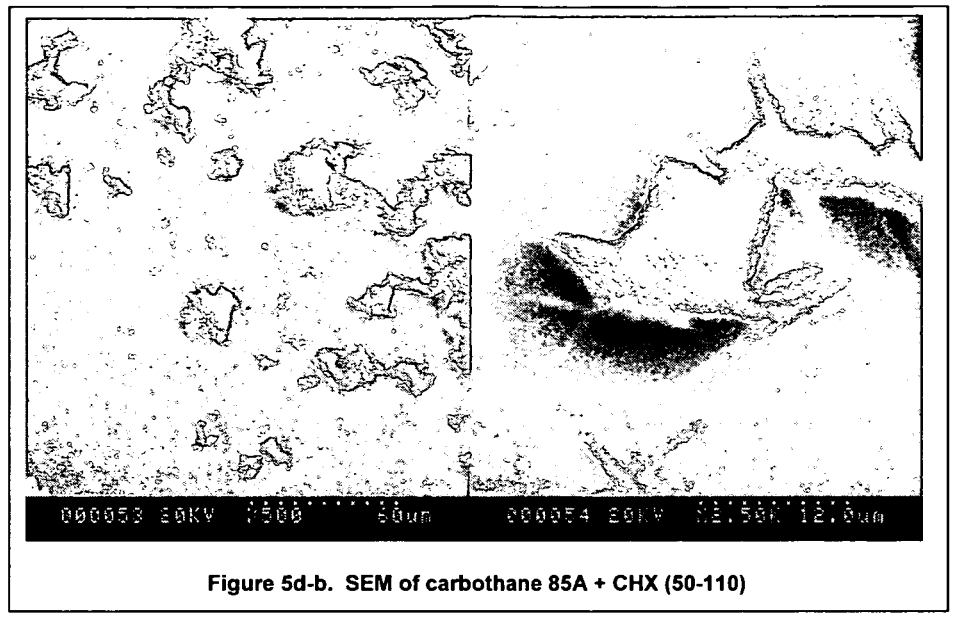
Figure 5d-b. SEM of carbothane 85A + CHX (50-110)
Fig. 5d(b)
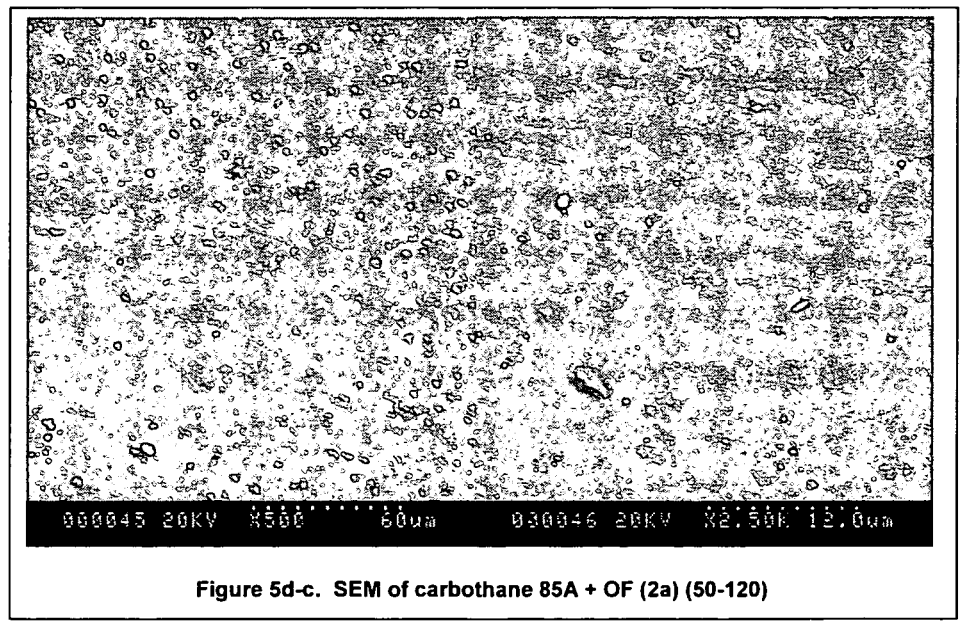
Figure 5d-c. SEM of carbothane 85A + OF (2a) (50-120)
Fig. 5d(c)

Figures 5d(e) and 5d(f)
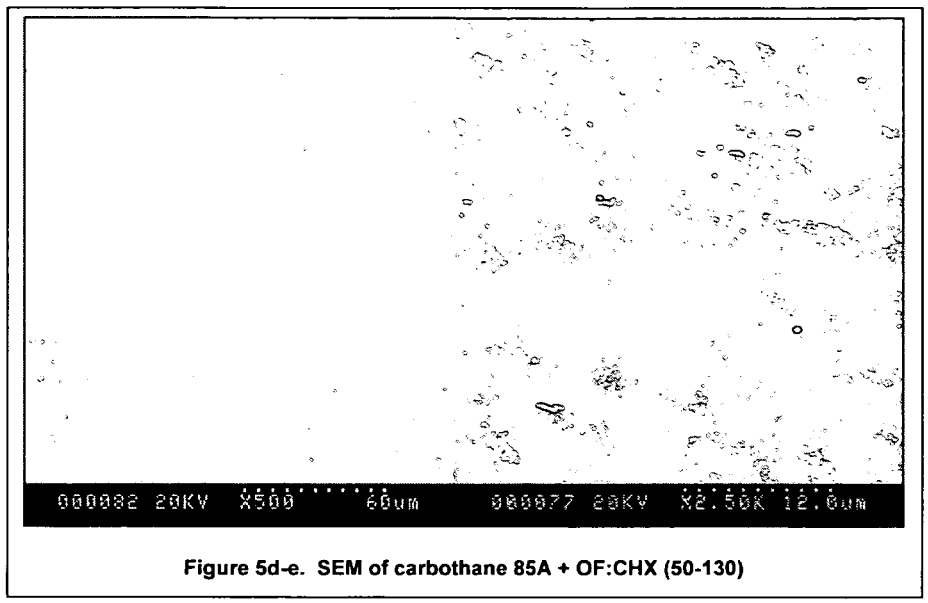
Fig. 5d(e)
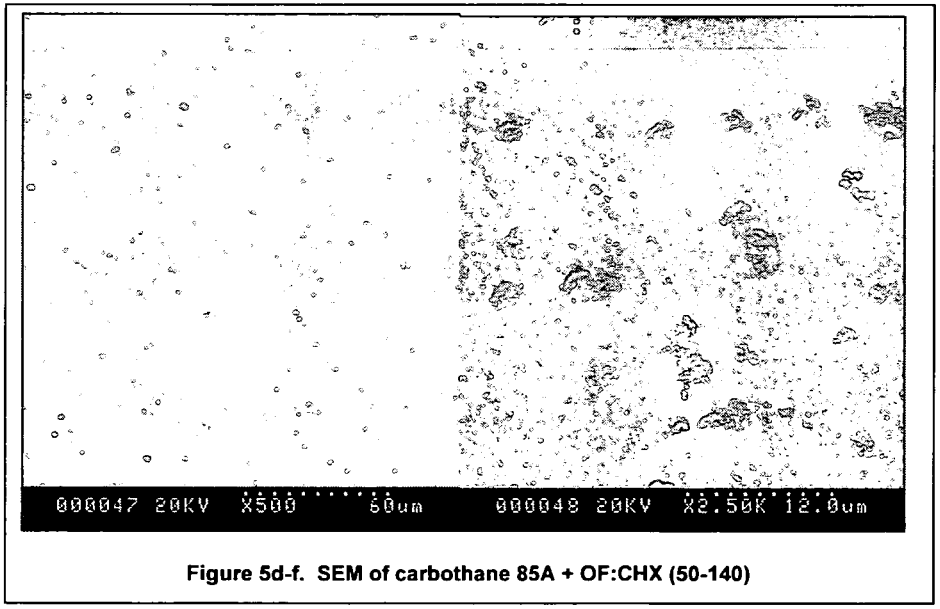
Fig. 5d(f)

Figure 5d(g) and 5d(h)
| Sample ID | C% | N% | O% | F% | Si% | Sn% | S% | Cl% |
|---|---|---|---|---|---|---|---|---|
| Carbothane 85A (50-100) | 84 | 4.1 | 10.7 | 0.1 | 1 | 0 | | |
| Carbothane 85A + CHX (50-110) | 66.7 | 15.2 | 12 | 0.4 | 1.8 | | 1 | 2.8 |
| Carbothane 85A + OF (50-120) | 45.9 | 3.1 | 13.5 | 37.1 | 0.1 | 0.4 | | |
| Carbothane 85A + (OF:CHX) (50-130) | 53.2 | 13.2 | 10 | 20.8 | 0.8 | 0 | | 2.7 |
| Carbothane 85A + (OF:CHX) (50-140) | 52.1 | 12.8 | 9.1 | 22.7 | 0.6 | 0 | | 2.7 |
Fig. 5d(g)
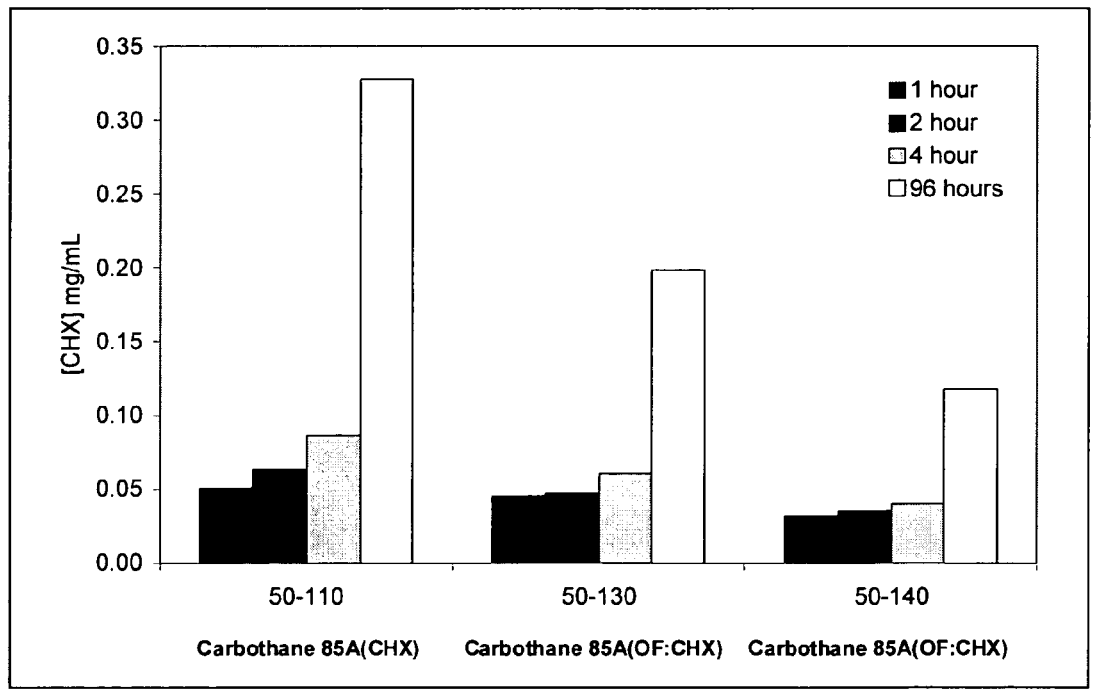
Fig. 5d(h)

Figures 6a and 6b
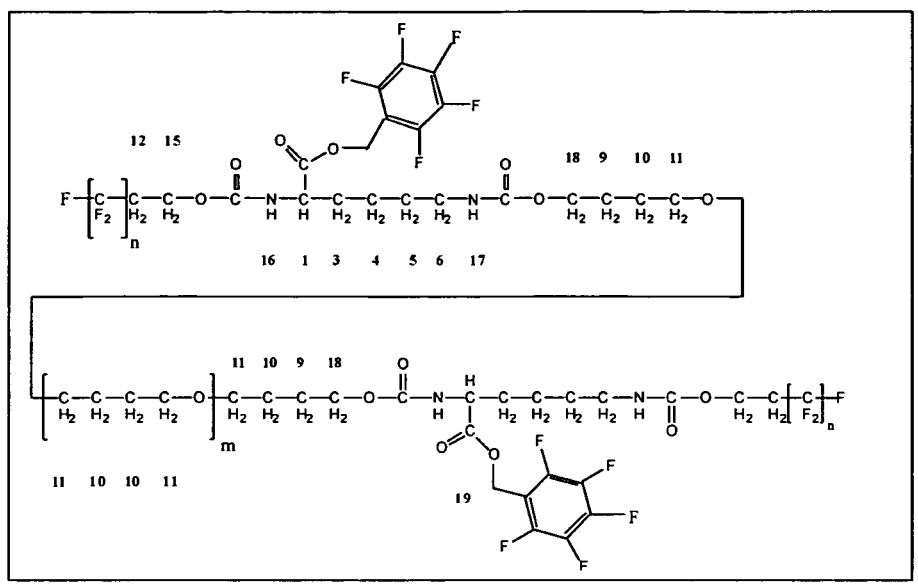
Fig. 6a
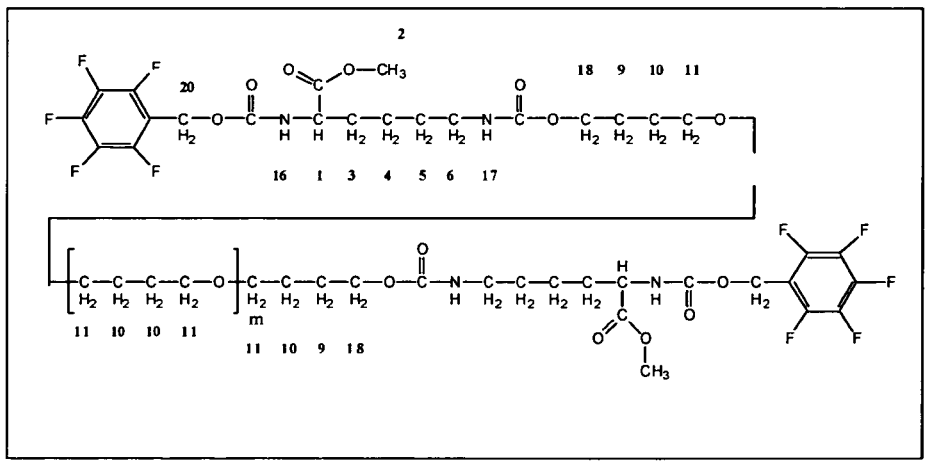
Fig. 6b

Figures 9a-c

OF 2a

Negative
(non-toxic)

Positive
(toxic)

METHODS AND COMPOSITIONS FOR THE DELIVERY OF BIOLOGICALLY ACTIVE AGENTS

CROSS-REFERENCE TO RELATED APPLICATIONS

This application claims benefit from U.S. Provisional Application No. 60/672,158, filed Apr. 14, 2005, hereby incorporated by reference.

BACKGROUND OF THE INVENTION

The invention relates to methods and compositions for the sustained release delivery of biologically active agents.

Polymeric materials have been widely used for manufacturing of medical devices, such as artificial organs, implants, medical devices, vascular prostheses, blood pumps, artificial kidney, heart valves, pacemaker lead wire insulation, intra-aortic balloon, artificial hearts, dialyzers and plasma separators, among others. The polymer used within a medical device must be biocompatible (e.g., must not produce toxic, allergic, inflammatory reactions, or other adverse reactions). It is the physical, chemical and biological processes at the interface, between the biological system and the synthetic materials used, which defines the short- and long-term potential applications of a particular device. In general, the exact profile of biocompatibility and biodegradation, including chemical and physical/mechanical properties i.e., elasticity, stress, ductility, toughness, time dependent deformation, strength, fatigue, hardness, wear resistance, and transparency for a biomaterial are extremely variable. To produce the desired properties, polymer blends produced through mixing, have been utilized. However, polymer mixing reduces entropy and induces phase separation. Thus, thermodynamic compatibility becomes an important factor for the functionality and stability of the polymer blend system.

The appropriate biological response to the surface of a device is crucial for biocompatibility. A practical approach taken towards the development of biomedical devices has involved the utilization of polymeric materials that satisfy the bulk material criteria for the device, while applying some form of surface modification. The ideal surface modification specifically tailors the biological surface properties and produces minimal change to the bulk character. Such an approach has advantages over grafting biologically active agents to the bulk polymer chains, since the latter approach brings about significant changes to the physical structure of the polymers. Methods that have been used for the surface modification of polymer surfaces, rather than bulk grafting of the polymers, have included the following: non-covalent coatings (with and without solvent), chemical surface grafting, ion implantation, Langmuir-Blodgett Overlayer and self assembled films, surface modifying additives, surface chemical reactions, and etching and roughening.

The polymeric coating of a medical device may also serve as a repository for delivery of a biologically active agent. Where the active agent is a pharmaceutical drug, it is often desirable to release the drug from the medical device over an extended period of time. Most systems for kinetically controlled direct drug delivery employ a polymer. For example, the agent may be released as the polymer enzymatically degrades or disintegrates in the body or may diffuse out of the polymeric matrix at a controlled rate. A site-specific drug transfer system can produce a high concentration of agent at the treatment site, while minimizing the adverse effects associated with systemic administration.

A polymeric system being used to control release of the drug must be free of impurities that trigger adverse biological responses (i.e., biologically inert), must produce the desired release profile, and must possess the mechanical properties required of the medical device.

In most cases biologically active agents are simply mixed with a polymer platform in a suitable solvent system. The biologically active agent is then released by particle dissolution or diffusion (when the non-bioerodable matrices are used) or during polymer breakdown (when a biodegradable polymer is used). Mixing lowers the entropy and this can result in phase separation throughout the bulk polymer, compromising the physical/mechanical properties of the polymeric coating.

U.S. Pat. No. 6,770,725 describes the covalent attachment of bioactive compounds to polymers with oligofluoro end groups. This approach was used to position biologically active agents at the surface of devices, to improve the biocompatibility of the device surface by modifying the surface with oligofluoro end groups, and to enhance the thermodynamic compatibility of the polymer-bioactive compound conjugate with the base polymer. The polymers described allow the base polymer to retain its bulk properties.

Covalent conjugation is often a multi-step chemical process ending with a covalent linkage between an available functional group in the polymer and a functional group in the biologically active agent. Generally, bioactive agents (i.e., drug) are structurally modified to accomplish covalent conjugation. For some biologically active agents, such modifications may result in the loss of some of the activity of the agent, or may completely inactivate the agent, making it impossible to deliver such an agent using a conjugation strategy.

In view of the potential drawbacks to current biologically active agent localization systems, there exists a need for surface modifying drug delivery platforms which provide for delivery of biologically active agents with a defined profile of release to targeted locations. The present invention addresses these problems and offers advantages over the prior art.

SUMMARY OF THE INVENTION

The invention provides polymer complexes for the delivery of biologically active agents. The complexes include at least one shielding moiety covalently tethered to at least one complexing moiety, which is complexed with at least one biologically active agent. The polymer complexes of the invention can provide surface properties that offset inflammatory responses and reduce thrombosis, and control the migration and release of biologically active agents when used, for example, to form the surface of an implanted device.

In a first aspect, the invention features a polymer including (i) a shielding moiety, (ii) an oligomeric segment, (iii) a complexing moiety, and (iv) a biologically active agent, wherein the shielding moiety and the complexing moiety are covalently tethered to the oligomeric segment and the complexing moiety is complexed with the biologically active agent.

In a related aspect, the invention features a polymer including (i) a shielding moiety, (ii) an oligomeric segment, (iii) a complexing moiety which provides two or more functional groups capable of forming non-covalent interactions with said biologically active agent, and (iv) a biologically active agent, wherein the shielding moiety and the complexing moiety are covalently tethered to the oligomeric segment and the complexing moiety is complexed with the biologically active agent.

In any of the above aspects, the polymer can include a complexing moiety which forms a non-covalent bonding interaction with the biologically active agent. Non-covalent bonding interactions include, without limitation, hydrogen bonding, ionic interactions, inclusion complexes, clathration, van der Waals interactions, and combinations thereof. Alternatively, the polymer can include a complexing moiety and biologically active agent coordinated to a metal center. The shielding moiety can be selected from, without limitation, polydimethylsiloxanes, hydrocarbons, fluorocarbons, fluorinated polyethers, polyalkylene oxides, and combinations thereof. The oligomeric segment may have an absolute molecular weight of greater than 10, 12, 14, 16, 18, or 20 kDa.

For any polymer of the invention, the oligomeric segment can include, without limitation, polyurethane, polyurea, polyamides, polyaklylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, polytetramethyleneoxide, or polyethylenebutylene segments.

For any polymer of the invention, from 0.1 to 5 weight % of the polymer can be complexing moiety and biologically active agent. Desirably, from 0.1 to 4, 0.1 to 3, 0.1 to 2, 0.5 to 5, or 1 to 5 weight % of the polymer is complexing moiety and biologically active agent.

For any polymer of the invention, the shielding moiety can be from about 0.01 to 5 weight % of the polymer. Desirably from 0.01 to 4, 0.01 to 3, 0.01 to 2, 0.01 to 1, 0.1 to 5, or 0.5 to 5 weight % of the polymer is shielding moiety.

For any polymer of the invention, the polymer can include a plurality of complexing moieties and a plurality of biologically active agents.

In an embodiment of any of the polymers above, the biologically active agent is selected from proteins, peptides, carbohydrates, antibiotics, antiproliferative agents, rapamycin macrolides, analgesics, anesthetics, antiangiogenic agents, vasoactive agents, anticoagulants, immunomodulators, cytotoxic agents, antiviral agents, antibodies, neurotransmitters, psychoactive drugs, oligonucleotides, proteins, vitamins, and lipids.

In another embodiment, from 0.1 to 99.9 weight % of the polymer can be complexing moiety and biologically active agent. Desirably, from 0.1 to 5, 1 to 10, 5 to 60, 50 to 90, or 60 to 99 weight % of the polymer is complexing moiety and biologically active agent.

In still another embodiment, the shielding moiety can be from about 0.1 to 30 weight % of the polymer. Desirably the shielding moiety is between 0.01 and 25, 0.01 and 20, 0.01 and 15, 0.01 and 5, 1 and 25, or 5 and 25 weight % of the polymer.

In one embodiment of the above aspects, the polymer is described by the formula:

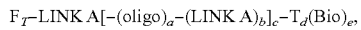

$$F_T\text{-LINK A}[-(\text{oligo})_a-(\text{LINK A})_b]_c-T_d(\text{Bio})_e,$$

wherein $F_T$ is a polyfluoroorgano group; Bio is one or more biologically active agents capable of being complexed to LINK A; each LINK A is, independently, an organic moiety including a complexing moiety which is capable of being complexed with a Bio; oligo is an oligomeric segment; T is a terminal group; a is 0 or 1; b, c, d, and e are integers greater than 0; and wherein at least one Bio is complexed to at least one LINK A. $F_T$ can be a polyfluoroalkyl, for example, $F_T$ can be selected from the group consisting of radicals of the general formula $CF_3(CF_2)_rCH_2CH_2—$ wherein r is 2-20, and $CF_3(CF_2)_s(CH_2CH_2O)_\chi$ wherein $\chi$ is 1-10 and s is 1-20.

Desirably, $F_T$ has a molecular weight of between 100-1,500 Da. Oligo can be a branched or non-branched oligomeric segment of not more than 20 repeating units. Oligo can be an oligomeric segment having an absolute molecular weight of greater than 10 kDa. LINK A can be a branched or non-branched oligomer of not fewer than 20 repeating units, or a monomeric segment. In one embodiment, a is 0.

In any of the above embodiments and aspects, the polymer can have the properties of a base polymer. Desirably, when the polymer functions as a base polymer, the oligomeric segment has an absolute molecular weight of greater than 10 kDa, 12 kDa, 14 kDa, 16 kDa, 20 kDa, 24 kDa, 28 kDa, 35 kDa, 50 kDa, 75 kDa, or even 100 kDa.

In any of the above embodiments and aspects, the polymer of the invention can include an oligomeric segment has an absolute molecular weight of less than about 10 kDa. This can be desirable where the polymer of the invention is used in an admixture.

In another aspect, the invention features an admixture including a polymer of the invention admixed with a base polymer.

In still another aspect, the invention features an admixture including a polymer admixed with a base polymer, wherein the polymer includes (i) a shielding moiety, (ii) a complexing moiety which provides two or more functional groups capable of forming non-covalent interactions with said biologically active agent, and (iii) a biologically active agent, wherein the shielding moiety is covalently tethered to the complexing moiety and the complexing moiety is complexed with the biologically active agent.

The invention also features a base polymer including (i) a biologically active agent having a release profile from the base polymer and (ii) a second polymer, wherein the second polymer includes (a) a shielding moiety, (b) an oligomeric segment, and (c) a complexing moiety,
wherein the shielding moiety and the complexing moiety are covalently tethered to the oligomeric segment and wherein the second polymer is present in an amount sufficient to alter the release profile.

The invention further features a base polymer including (i) a biologically active agent having a release profile from the base polymer and (ii) a second polymer, wherein the second polymer includes (a) a shielding moiety, (b) an oligomeric segment, and (c) a complexing moiety which provides two or more functional groups capable of forming non-covalent interactions with the biologically active agent, and wherein the shielding moiety and the complexing moiety are covalently tethered to the oligomeric segment and wherein the second polymer is present in an amount sufficient to alter the release profile.

For any admixture of the invention, the admixture can include from 0.1 to 10 weight % polymer complex. Desirably the admixture is between 0.01 and 15, 0.01 and 10, 0.1 and 5, 1 and 15, 1 and 10, or 1 and 5 weight % polymer complex.

Exemplary base polymers for use in the admixtures of the invention include, without limitation, polyurethanes, polysulfones, polycarbonates, polysaccharide, polyesters, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinyl chloride, polyethylene terephthalate, cellulose and its esters and derivatives, polyamides, polyester-polyethers, styrene-isoprenes, styrene butadienes, thermoplastic polyolefins, styrene-saturated olefins, polyester-polyester, ethylene-vinyl acetate ethylene-ethyl acrylate, ionomers, thermoplastic polydienes, and combinations thereof.

The invention also features a shaped article formed from a polymer complex of the invention.

The invention further features a shaped article formed from an admixture of the invention.

In another aspect, the invention features a shaped article comprising a polymer of the invention. Desirably, the article is coated with the polymer of the invention.

The article of the invention can be any implantable medical device, such as a cardiac-assist device, a catheter, a stent, a prosthetic implant, an artificial sphincter, or a drug delivery device.

In some embodiments, articles of the invention release 80% of the releasable biologically active agent within 2 years.

The articles of the invention can have a release profile for a biologically active agent in which $t_{50}$ is greater than 6 months. Desirably, $t_{50}$ is greater than 9 months, 1 year, 2 years, or even 5 years.

The articles of the invention can have a release profile for a biologically active agent in which $t_{10}$ is greater than 1/10 of $t_{50}$.

In another aspect, the invention features a composition for delivery of a biologically active agent including a polymer complex as described herein, wherein the composition is formulated in the absence of a device, e.g., in a cream, gel, or lotion for, e.g., topical application in the absence of, during, or following a medical procedure.

The invention further features a composition for controlling the proliferation of pests (e.g., insects or weeds) including a polymer complex as described herein, wherein the biologically active agent is a pesticide (e.g., an insecticide) or herbicide.

The invention also features a composition for reducing microbial growth on a surface including a polymer complex of claim 1, wherein the biologically active agent is an antimicrobial agent.

In another aspect, the invention features a method of reducing inflammation at a site in a mammal in need thereof. The method includes implanting an article of the invention at the site, wherein the polymer complex includes an anti-inflammatory agent which is released from the surface of the article in an amount sufficient to reduce inflammation. Useful anti-inflammatory agents include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, tolmetin, algestone, amcinonide, beclomethasone, betamethasone, budesonide, clobetasol, corticosterone, cortisone, dexamethasone, flucloronide, hydrocortisone, prednisolone, and triamcinolone, or combinations of these and other biologically active agents.

In a related aspect, the invention features a method of reducing restenosis at a site in a mammal in need thereof. The method includes implanting an article of the invention at the site, wherein the polymer complex includes an anti-proliferative agent which is released from the surface of the article in an amount sufficient to reduce restenosis. Useful anti-proliferative agents include, without limitation, rapamycin, CCI-779, Everolimus, ABT-578, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™, leflunomide, SU5416, SU6668, PTK787 (Novartis), Iressa™ (AstraZeneca), Tarceva™, trastuzumab, Erbitux™, PKI166, GW2016, EKB-509, EKB-569, MDX-H210, 2C4, MDX-447, ABX-EGF, CI-1033, Avastin™, IMC-1C11, ZD4190, ZD6474, CEP-701, CEP-751, MLN518, PKC412, 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026, DHA-paclitaxel, Taxoprexin, TPI-287, Sphingosine-based lipids, and mitotane.

The invention also features a method of reducing pain at a site in a mammal in need thereof. The method includes implanting an article of the invention at the site, wherein the polymer complex includes an analgesic or anesthetic agent which is released from the surface of the article in an amount sufficient to reduce pain. Useful analgesic agents include, without limitation, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine, and dihydroacetorphine. Useful anesthetic agents include, without limitation, cocaine, procaine, lidocaine, prilocaine, mepivicaine, bupivicaine, articaine, tetracaine, chloroprocaine, etidocaine, and ropavacaine.

The invention further features a method of relaxing muscle at a site in a mammal in need thereof. The method includes implanting an article of the invention at the site, wherein the polymer complex includes an antispasmodic agent which is released from the surface of the article in an amount sufficient to relax muscle. Useful antispasmodic agents include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

In all of the above embodiments and aspects, the biologically active agent may be provided as a prodrug, e.g., a amide or ester of the biologically active agent.

In another aspect, the invention features a method for controlling the release of a biologically active agent from the surface of a shaped article by (i) complexing the biologically active agent with a polymer of the invention to form a polymer complex, and (ii) using the polymer complex to form the surface of said article, wherein the polymer complex includes from about 0.1 to 30 weight % shielding moiety.

In another aspect, the invention features a method for controlling the release of a biologically active agent from the surface of a shaped article. The method includes (i) forming a shaped article comprising a biologically active agent, and (ii) coating the surface of the shaped article with a polymer of the invention.

Any suitable chain ending terminal group $T_d$, e.g., a radical, may be present in the polymers of the invention including, without limitation, H, alkyl, ester, hydroxyl, and shielding moieties.

By "amount sufficient" is meant the amount of biologically active agent necessary to achieve a desired result. The amount sufficient will vary depending upon a variety of parameters, including the condition being treated (e.g., pain, pest control, or microbial growth, among others), the site being treated, the biologically active agent selected, the polymer complex selected, and the delivery vehicle employed (e.g., implanted device, cream, or pellet, among others). A sufficient amount can be determined for any given set of conditions using standard methods. For example, the release of biologically active agent from a surface can be monitored as a function of the parameters above. Based upon these results, a vehicle prepared which releases the agent at a rate that produces the desired effect.

By "base polymer" is meant a polymer having a tensile strength of from about 350 to about 10,000 psi, elongation at break from about 300% to about 1500%, an unsupported thickness of from about 5 to about 100 microns, and a supported thickness of from about 1 to about 100 microns.

By "biologically active agent" is meant a compound, be it naturally-occurring or artificially-derived, that is complexed with a polymer of the invention and which may be released and delivered to a specific site. Biologically active agents may include, for example, peptides, proteins, synthetic organic molecules, naturally occurring organic molecules, nucleic acid molecules, and components thereof. Desirably, the biologically active agent is a compound useful for the therapeutic treatment of a plant or animal when delivered to a site of diseased tissue. Alternatively, the biologically active agent can be selected to impart non-therapeutic functionality to a surface. Such agents include, for example, pesticides, bactericides, fungicides, fragrances, and dyes.

As used herein, "complexed" or "complexation" refers to an interaction, either non-covalent or via coordination to a metal center, between the complexing moiety in a polymer of the invention and a biologically active agent. Examples of non-covalent bonding interactions which can be used in accordance with the present invention include, without limitation, hydrogen bonding, ionic interactions (e.g., dipole-dipole interactions, ion pairing, and salt formation), inclusion complexes, clathration, van der Waals interactions (e.g., pi-pi stacking), and combinations thereof. The interaction can also be via coordination to a metal center by both the complexing moiety and the biologically active agent. In some instances, the biologically active agent includes a metal center which is coordinated to the complexing moiety.

As used herein, "complexing moiety' refers to that portion of the polymer of the invention which complexes the biologically active agent either via a non-covalent interaction or coordination to a metal center, forming a polymer complex. The complexing moiety can be a charged moiety, e.g., a moiety which loses a proton at physiological pH thereby becoming negatively charged (e.g., carboxylate, or phosphodiester), a moiety which gains a proton at physiological pH thereby becoming positively charged (e.g., ammonium, guanidinium, or amidinium), a moiety that includes a net formal positive charge without protonation (e.g., quaternary ammonium), or a moiety that includes a net formal negative charge without loss of a proton (e.g., borate, $BR4^-$). Exemplary charged complexing moieties include, without limitation, carboxylate, phosphodiester, phosphoramidate, borate, phosphate, phosphonate, phosphonate ester, sulfonate, sulfate, thiolate, phenolate, ammonium, amidinium, guanidinium, quaternary ammonium, and imidazolium functionalities. The complexing moiety can be designed to physically encapsulate, in whole or in part, the biologically active agent, such as a cyclodextrin. The complexing moiety be designed to ligate a complementary oligonucleotide and/or peptide sequence present in the biologically active agent. The complexing moiety can be designed to coordinate a metal center including the biologically active agent, either as a ligand alone or including the metal center.

As used herein, "covalently tethered" refers to moieties separated by one or more covalent bonds. For example, where a shielding moiety is covalently tethered to a complexing moiety, tethered includes the moieties separated by a single bond as well as both moieties separated by an oligomeric segment to which both moieties are covalently attached.

As used herein, "polymer complex" refers to a polymer complexed with a biologically active agent. Polymer complexes may comprise oligomeric segments which have the properties of a base polymer and are useful, by themselves, for forming shaped articles. Alternatively, polymer complexes may be relatively low molecular weight compounds of less than 20 kDa, making them useful additives to base polymer systems. Low molecular weight polymer complexes can more readily diffuse among the macromolecular polymer chains in an admixture of the polymer complex with a base polymer.

By "prodrug" is meant a precursor to a biologically active agent which is converted in vivo, e.g., by enzymatic and/or hydrolytic mechanisms, into a biologically active agent. Prodrugs include, without limitation, esterified biologically active agents.

As used herein, "shielding moiety" refers to a lipophilic tail of a polymer of the invention. Shielding moieties are covalently attached to the polymer of the invention at a single point, for example, capping the end of the polymer, or attached to a branching point in the middle of the polymer. Furthermore, the shielding moiety can be selected to be incompatible with a base polymer, i.e., when admixed therewith to form an article, to cause migration of the polymer complex to the surface of an article of the invention. Shielding moieties can be selected to alter the release profile of the biologically active agent. Shielding moieties can also reduce degradation of the biologically active agent in vivo and/or during the manufacture of articles of the invention. Shielding moieties include, without limitation, polydimethylsiloxanes, hydrocarbons, fluorocarbons, fluorinated polyethers, polyalkylene oxides, fluorinated aryls, and combinations thereof.

As used herein, "altering the release profile" refers to a change of 10%, 20%, 30%, 40%, or even 50% in the $t_{50}$ for the release of a biologically active agent from an article of the invention in comparison to the same article free of a polymer of the invention.

As used herein, "$t_{50}$" is the time at which 50% of the releasable biologically active agent has been released from an article of the invention. Time $t_{10}$ is, correspondingly, the time at which 10% of the releasable biologically active agent has been released. When the release curve is perfectly linear, $t_{10}=\frac{1}{5}$ of $t_{50}$. When there is an initial burst of released agent, $t_{10}$ is much less than $\frac{1}{5}$ of $t_{50}$. In the methods and articles of the invention $t_{10}$ can be greater than $\frac{1}{10}$ of $t_{50}$. Thus, there can be little or no initial burst of release of the biologically active agent. The releasable biologically active agent is the amount that is released from an article in a period of time 10 times greater than the period of time it takes for 10% of the incorporated agent to be released in phosphate buffered saline at pH 7.4.

The following acronyms denote the listed compounds used in the preparation of the polymer complexes described herein.

| | |
|---|---|
| LDI | lysine diisocyanate |
| HDI | 1,6 hexamethylene diisocyanate |
| DABS | 2,5 diaminobenzenesulfonic acid |
| PCN | polycarbonate diol |
| PPO | polypropylene oxide diol |
| MDI | methylene diphenyl diisocyanate |
| PTMO | polyethylene tetramethylene oxide |
| PCN | polycarbonate diol |
| PDMS | (polydimethylsiloxane-bis (3-aminopropyl) terminated) |
| PHE | (amine terminated oligo-phenylalanine) |
| PEB | (polyethylene-butylene co-polymer diol) |
| THDI | trimethyl-1,6 diisocyanatohexane |
| DPS | dihydroxy diphenylsulfone |
| PD | 1,5 pentanediol |
| HDI/PCN/BD | segmented polyurethane |
| DMAc | dimethylacetamide |
| DMF | dimethylformamide |
| Fluoroalkyl | Fluoro compounds with function terminal groups such as (OH, $NH_2$, COOH, NCO) |
| TMPP | 5,10,15,20-tetrakis(methyl-4-pyridyl)21H,23H porphine-tetra-p-tosylate salt |

The methods and compositions of the present invention allow the biologically active agent to be complexed with a polymer of the invention without chemical modification of the agent. Furthermore, because the biologically active agent is non-covalently complexed with the polymer, the release of the agent is facile under aqueous conditions.

Other features and advantages of the invention will be apparent from the following Detailed Description, the drawings, and the claims.

BRIEF DESCRIPTION OF THE DRAWINGS

FIG. 1*a* depicts the structure of 5,10,15,20-tetrakis (4-N-methylpyridyl-Porphyrin)-TMPP complexed with $F_T$([HDI-DABS][PTMO]).

FIGS. 1*b*-1*e* are graphs showing the release profile analysis for TMPP in various conditions (e.g., acidic, basic, and neutral conditions).

FIGS. 2*a*-2*d* are images from polarized light (PL) microscopy of various mixtures. FIG. 2*a* is the PL micrograph of the polymer 2*a*. It depicts the featureless characteristics of the compound. FIG. 2*b* is the PL micrograph of the ceramide. It depicts the crystal lattice formation of the compound. FIG. 2*c* is the PL micrograph of the mixture as control. It depicts phase separation nature of the mixture. It also indicates the heterogenous nature of the mixture. FIG. 2*d* is the PL micrograph of the complex. It depicts the homogenous nature of the end product.

FIGS. 2*e*-2*h* are images from scanning electron microscopy (SEM) of various mixtures. FIG. 2*e* is the scanning electron micrograph of the polymer 2*a*. It depicts the featureless characteristics of the compound. FIG. 2*f* is the scanning electron micrograph of the ceramide. FIG. 2*g* is the scanning electron micrograph of the mixture as control. It depicts the heterogenous characteristics of the product. Phase separation is also observed. FIG. 2*h* is the scanning electron micrograph of the complex. It depicts the homogenous nature of the end product.

FIGS. 2*i* and 2*j* are images from scanning electron microscopy of stainless steel unpolished metallic platforms coated with a thin layer of C6-Ceramide-$F_T$([LYS][PTMO]) complex. The results show a homogenous coating is formed.

FIG. 2*k* depicts a differential scanning calorimetric graph of the C6-Ceramide-$F_T$([LYS][PTMO]) complex.

FIG. 2*l* shows the HPLC data indicating that the primary structure of the active compound remains unchanged after complexation and decomplexation.

FIGS. 2*m*-2*p* are images from scanning electron microscopy of a coated prototype device showing that no phase separation is observed for the complex.

FIG. 2*q* is an ideal structure for the methyl ester of compound 2a.

FIG. 3*a* is an ideal structure for compound 3a.

FIG. 3*b* depicts the 6-Monodeoxy-6-monoamino-β-cyclodextrin backbone with atom positions labeled.

FIG. 4*a* is a scheme depicting Cisplatin hydrolysis products and intermediates.

FIG. 4*b* is a graph depicting the release profile for Cisplatin complexed with $F_T$([LYS($COO^-Na^+$)][PTMO]).

FIG. 5*a* depicts the structure of Chlorhexidine.

FIGS. 5*d*(*a*)-5*d*(*f*) are images from scanning electron microscopy of films made from Carboethane (FIG. 5*d*(*a*) control), Chlorhexidine in Carboethane (FIG. 5*d*(*b*) showing crystallization of the drug at the surface and lack of a homogenous platform), $F_T$([LYS][PTMO]) in Carboethane (FIG. 5*d*(*c*) control), and Chlorhexidine-$F_T$([LYS][PTMO]) complex in Carboethane (FIGS. 5*d*(*e*) and 5*d*(*f*), showing a homogenous platform with no phase separation).

FIG. 5*d*(*g*) is a table of XPS data of for carbothane films (90° take-off) showing that percentage of fluorine in the top 10 nm, indicating the migratory property of $F_T$([LYS][PTMO]), and the percentage of chlorine in the top 10 nm, indicating the presence of Chlorhexidine.

FIG. 5*d*(*h*) is a table showing the release of Chlorhexidine from strips of film placed in water. This data showed the differences in CHX release profile and the ability of the drug delivery platform to allow release (i.e., dissociation from the delivery platform).

FIG. 6*a* is an ideal structure for compound 6a ($F_T$([LDI](PFB)[PTMO])).

FIG. 6*b* is an ideal structure for compound 6b ($F_T$(PFB)([LDI][PTMO])).

FIG. 6*h* is a graph depicting the release profile of ibuprofen as described in Example 6 for 6c (a complex of (6a):Ibuprofen), 6d (a complex of (6b):Ibuprofen), and 6e (a complex of (2a):Ibuprofen). The data illustrate the design of a delivery system suitable for interaction with Ibuprofen, via p-p stacking and a release profile showing the ability of the drug to dissociate from the delivery platform.

FIG. 7*a* is an ideal structure for compound 7 ($F_T$([LYS(Tris)][PTMO])).

FIGS. 8*c* and 8*d* are graphs depicting the release profile for salicylic acid from polycaprolactone films as described in Example 8.

FIGS. 9*a*-9*c* are images showing the direct contact cytotoxicity assay (FIG. 9*a*) along with a positive (FIG. 9*c*) and negative (FIG. 9*b*) controls. Following incubation, viable cells are identified by a positive purple stain and the cytotoxicity was determined by examining the stained filter for cell exclusion zones around the cast material, or a low cell density.

DETAILED DESCRIPTION

The methods and compositions of the invention allow for surface modification in a controlled manner, while maintaining the desired bulk properties of a base polymer. The surface modification results from interfacial energy minimization and, using the methods and compositions of the invention, can be used to formulate specialized materials for specific applications. For example, surface modifications can be designed to alter the surface chemical composition, hydrophobicity, biocompatibility, and/or adhesion characteristics. Furthermore, bulk surface rearrangements (relaxation, segregation, and reconstruction), including "chemical" changes, due to diffusion and/or transformation of surface atoms or molecules, can be controlled using surface modification processes described herein.

The invention features polymer complexes for the delivery of biologically active agents. The polymer complexes can be designed to deliver a wide variety of biologically active agents. The methods and compositions require no structural alteration of the agent being delivered. Furthermore, the release of the agent at a surface does not necessarily depend upon in vivo biodegradation processes. Accordingly, the methods and compositions of the present invention can be used to deliver biologically active agents to non-biological sites.

Polymers and Polymer Complexes

The polymers of the invention include a shielding moiety covalently tethered to a complexing moiety. The complexing moiety is capable of forming a complex with a biologically active agent via non-covalent interactions or by coordination to a metal center. A variety of non-covalent interactions can be utilized in the formation of complexes between a biologically active agent and polymer of the invention, including hydrogen bonding, ionic interactions, inclusion complexes, clathration, van der Waals interactions, and combinations thereof. The shielding moiety is a lipophilic tail that can shield the biologically active agent from degradation (e.g., enzymatic and/or environmental decomposition) and/or can carry the polymer complex to a surface, altering the surface properties and releasing the biologically active agent. The chemical composition and molecular weight of the shielding moiety, as well as the structure of the biologically active agent, are generally the controlling factors in directing the shielding effect.

The polymer complex allows uniform topography and stratification of the biologically active agent within the base polymer (e.g., either the polymer complex itself, or an admixture of polymer complex and base polymer) and, ultimately, controlled delivery at the targeted location. Furthermore, this design provides interfacial compartments or immobilization of the biologically active compound in discrete and defined complexes that are uniformly distributed.

The amount of biologically active agent loaded onto the polymer complex will depend upon the design of the polymer in combination with the desired release profile. The composition of the polymer may be designed for the particular agent being delivered and to provide the mechanical properties necessary for the particular application.

The process by which the polymer complex is formed may be a two or multi-step procedure that produces a homogenous matrix. In general, polymers and polymer complexes of the invention can be prepared as described in the Examples.

Biologically Active Agents

Biologically active agents that can be incorporated polymer complexes of the invention include therapeutic, diagnostic, and prophylactic agents. They can be naturally occurring compounds, synthetic organic compounds, or inorganic compounds. Agents that can be incorporated into the polymer complexes of the invention include, but are not limited to, proteins, peptides, carbohydrates, antibiotics, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogrel and ramatroban, ananti-bodies, neurotransmitters, psychoactive drugs, oligonucleotides, proteins, lipids, and combinations thereof.

Exemplary therapeutic agents include growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutytric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active agent can be an antiinflammatory agent, such as an NSAID, corticosteriod, or COX-2 inhibitor, e.g., rofecoxib, celecoxib, valdecoxib, or lumiracoxib.

Exemplary diagnostic agents include imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials.

A preferred biologically active agent is a substantially purified peptide or protein. Proteins are generally defined as consisting of 100 amino acid residues or more; peptides are less than 100 amino acid residues. Unless otherwise stated, the term protein, as used herein, refers to both proteins and peptides. The proteins may be produced, for example, by isolation from natural sources, recombinantly, or through peptide synthesis. Examples include growth hormones, such as human growth hormone and bovine growth hormone; enzymes, such as DNase, proteases, urate oxidase, alronidase, alpha galactosidase, and alpha glucosidase; antibodies, such as trastuzumab.

Rapamycin Macrolides

Rapamycin (Sirolimus) is an immunosuppressive lactam macrolide that is produced by *Streptomyces hygroscopicus*. See, for example, McAlpine, J. B., et al., *J. Antibiotics* 44: 688 (1991); Schreiber, S. L., et al., *J. Am. Chem. Soc.* 113: 7433 (1991); and U.S. Pat. No. 3,929,992, incorporated herein by reference. Exemplary rapamycin macrolides which can be used in the methods and compositions of the invention include, without limitation, rapamycin, CCI-779, Everolimus (also known as RAD001), and ABT-578. CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Antiproliferative Agents

Exemplary antiproliferative agents which can be used in the methods and compositions of the invention include, without limitation, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™ (Novartis), leflunomide (Pharmacia), SU5416 (Pharmacia), SU6668 (Pharmacia), PTK787 (Novartis), Iressa™ (AstraZeneca), Tarceva™, (Oncogene Science), trastuzumab (Genentech), Erbitux™ (ImClone), PKI166 (Novartis), GW2016 (GlaxoSmithKline), EKB-509 (Wyeth), EKB-569 (Wyeth), MDX-H210 (Medarex),2C4 (Genentech), MDX-447 (Medarex), ABX-EGF (Abgenix), CI-1033 (Pfizer), Avastin™ (Genentech), IMC-1C11 (ImClone), ZD4190 (AstraZeneca), ZD6474 (AstraZeneca), CEP-701 (Cephalon), CEP-751 (Cephalon), MLN518 (Millenium), PKC412 (Novartis), 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026DHA-paclitaxel, Taxoprexin, TPI-287, Sphingosine-based lipids, and mitotane.

Corticosteroids

Exemplary corticosteroids which can be used in the methods and compositions of the invention include, without limitation, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, predinval, prednylidene, prednylidene 21-diethylaminoacetate, tixocortol, triamcinolone, triamcinolone acetonide, triamcinolone benetonide and triamcinolone hexacetonide. Structurally related corticosteroids having similar anti-inflammatory properties are also intended to be encompassed by this group.

NSAIDs

Exemplary non-steroidal antiinflammatory drugs (NSAIDs) which can be used in the methods and compositions of the invention include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

Analgesics

Exemplary analgesics which can be used in the methods and compositions of the invention include, without limitation, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine and dihydroacetorphine.

Antimicrobials

Exemplary antimicrobials which can be used in the methods and compositions of the invention include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Local Anesthetics

Exemplary local anesthetics which can be used in the methods and compositions of the invention include, without limitation, cocaine, procaine, lidocaine, prilocaine, mepivicaine, bupivicaine, articaine, tetracaine, chloroprocaine, etidocaine, and ropavacaine.

Antispasmodic

Exemplary antispasmodics which can be used in the methods and compositions of the invention include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

Admixtures with Base Polymers

Where the polymer complex does not have base polymer properties, it may be desirable to prepare an admixture with a base polymer to produce the requisite mechanical properties, e.g., for a shaped article. Desirably, the polymer complex is concentrated within the nm region of the exterior polymer interface and is designed to be thermodynamically compatible with the base polymer to prevent phase separations.

Many materials having base polymer properties are known in the art. Base polymers useful in the admixtures of the invention can include, without limitation, polyurethane, polysulfones, polycarbonates, polysaccharides, polyesters, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinyl chloride, polyethylene-terephthalate, cellulose and its esters and derivatives, polyamides, polyester-polyethers, styrene-isoprenes, styrenebutadienes, thermoplastic polyolefins, styrene-saturated olefins, polyester-polyester, ethylene-vinyl acetate ethylene-ethyl acrylate, ionomers, and thermoplastic polydienes.

Shaped Articles

Articles of the invention can be formed from polymer complexes used either alone or as an admixture with a base polymer. One advantage of using a polymer complex alone as the base polymer to form a shaped article is that because there is no polymer mixing, there is no reduction in entropy and no possibility of phase separation.

Any shaped article can be made using the compositions of the invention. For example, articles suitable for contact with bodily fluids, such as medical can be made using the compositions described herein. The duration of contact may be short, for example, as with surgical instruments or long term use articles such as implants. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillarors, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

An implantable medical device as described above is generally structured from a base metallic or polymeric platform in a solid state format. The polymer complex within this primary platform, either alone or as an admixture, controls the release of therapeutic agents from the device.

The methods and compositions of the invention can also be used to deliver a biologically active agent to the surface of a cosmoceutical (e.g., creams, gels, and lotions), to a pellet, e.g., for controlling the proliferation of pests, such as weeds or insects, or to a membrane, for example, for use in a water purification process in which an antibacterial agent is released into the water.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

GENERAL EXPERIMENTAL PROTOCOLS

Purification: A number of purification techniques have been used in the experimental section. A brief summary of each technique is noted below:

Dialysis: Size exclusion purification is where a membrane separates molecules based on their size in solution. Lower molecular weight molecules pass through dialysis membranes into a large volume of solvent. In this series of experimental protocols the membrane used was SpectraPor 6 Regenerated Cellulose (RC).

Column Chromatography: The stationary phase used for column chromatography is typically silica gel. In general Fluorinated compounds do not interact with silica. This allowed for a rapid filtration of smaller molecules.

Solid Phase Extraction (Cationic): A pre-packed cationic silica gel column (plastic) was used to remove small cationic compounds from the reaction mixtures.

Ultrafiltration (Centricon and Pellicon): This technique is based on a separation process, using a semi-permeable membrane to separate large molecules from small compounds. A solution of OF was pressurized over a membrane using tangential flow to separate larger molecules from smaller ones.

Fluorous Solid Phase Extraction (F-SPE): SPE substrates modified with perfluorinated ligands (F-SPE) were used to selectively retain the OF, allowing the separation of non-fluorinated compounds.

Cytotoxicity Assay: Polymeric compounds synthesized in the experimental section were profiled for cytotoxicity. A brief description of the test is summarized as follows.

Figure 9A:
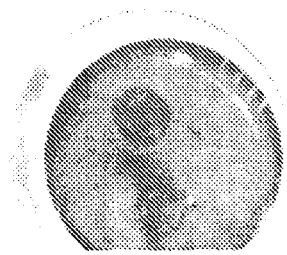
Figure 9B:
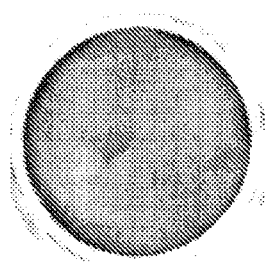
Figure 9C:
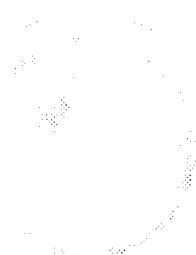

Direct Contact Cytotoxicity Assay: The viability of HeLa epithelial cells in direct contact with test materials was used to assess the potential cytotoxicity of oligofluoro (OF). A sample of test material was solvent cast on an agar-supported Supor filter. Subsequently, a monolayer of HeLa cells were cultured directly on the filter, in the presence of MEM culture media. After 24 hours of incubation, the Supor filter was rinsed and stained with succinic dehydrogenase. Viable cells were identified by a positive purple stain and the cytotoxicity was determined by examining the stained filter for cell exclusion zones around the cast material, or a low cell density. Each cytotoxicity assay included a positive and negative control, as depicted in FIGS. 9A-C, which shown example of Supor filters that have been stained to mark viable HeLa cells.

EXAMPLE 1

$F_T([HDI-DABS][PTMO]):TMPP$

1a: Synthesis of $F_T([HDI-DABS][PTMO])$

Polytetramethyleneoxide (PTMO) (predried, 10 g) was dissolved in dimethylacetamide (DMAc) (50 mL). A freshly prepared solution of 1,6-hexane diisocyanate (HDI) and 2,5-diaminobenzenesulfonic acid (DABS) (9.2 g) in DMAc (50 ml) was reacted with the solution of PTMO under an atmosphere of nitrogen for two hours. Fluoro alcohol (11.7 g)

dissolved in DMAc (30 mL) was added to the reaction mixture. Dibutyltin dilaurate was used as a catalyst. The reaction mixture was sealed and kept under nitrogen and the temperature was maintained between 60-70° C. for 2.5 hours. Purification was achieved by a precipitation technique. The end product was dried in a vacuum oven for 24 hours. The XPS analysis area was 700×300 microns in size with the following atomic content, C(50.9%), N(7.0%), O(19.7%), S(1.2%) with a total fluorine content of (21.2%), by weight. The IR analysis was in accordance with the chemical structure 3349.68 (cm$^{-1}$), ν(N—H), H-bonded, 2927.20 (cm$^{-1}$), ν(C—H), CH2 asymmetric stretching, 2855.41 (cm$^{-1}$), ν(C—H), CH$_2$ symmetric stretching, 1740 (cm$^{-1}$), ν(C=C), urethane Non-bonded, 1700 (cm$^{-1}$), ν(C—O), urethane H-bonded, 1452.19 (cm-1), ν(C=C), aromatic ring, 1493.40 (cm$^{-1}$), ν(C—C), aromatic ring, 1208.10 (cm$^{-1}$), ν(S=O), 1400-1000 ν(C—F), monofluoroalkanes absorb to the right in the range, while polyfluoroalkanes give multiple strong bands over the range from 1350-1100 (cm$^{-1}$). NMR analysis was used for comparison of the aromatic region before and after conjugation. Elemental analysis $C_{120}H_{186}O_{31}N_{12}S_2F_{34}$ was in accordance with the expected structure [% C, 48.00% (52.63% (+4.63%)), % H, 7.88% (6.24% (+1.64%)), % N, 6.95% (5.6% (+1.35%)), % F, 6.48% (21.51% (−15.03%)), % S, 2.14% (2.58% (−0.44%)).

1b: Complex Formation, Isolation and Release Profile—5,10,15,20-tetrakis(methyl-4-pyridyl)21H,23H porphine-tetra-p-tosylate salt (TMPP).

To a solution of surface modifier (1a) (0.262 g) in dimethylsulfoxide (DMSO) (5 ml) was added 5,10,15,20-tetrakis (methyl-4-pyridyl)21H,23H porphine-tetra-p-tosylate salt (TMPP) (0.0198 g., 1 mL DMSO). The reaction mixture was sealed and left under nitrogen for 24 hours. The dimethylsulfoxide was removed under reduced pressure (50° C., 10$^{-1}$ mm Hg) forcing the formation of the desired complex. The excess TMPP was washed using phosphate buffer (pH=7, 3×20 mL). The end product was dried under vacuum. To illustrate the complex formation and the release profile a comprehensive ultraviolet analysis (λ=443 nm), using different media to monitor the kinetics of dissociation, was performed. It is important to note that when the reaction was completed in a mixed solvent system (H$_2$O(50):DMAc(50)) the release profile was indicative of a dumping style (one time release) (t=5 min, A=0.3184; t=70 min, A=3.014; t=146 min, A=3.9677; t=203 min, A=3.9587; t=364 min, A=4.0284] (FIG. 1b). Hence, for the complex to be formed a suitable solvent system is an essential requirement. HCl (1M) (t=5 min, A=0.1124), (t=67 min, A=0.3549), (t=72 min, A=0.3132), (t=132 min, A=0.3342), (t=187 min, A=0.3903), (t252 min, A=0.4740) (FIG. 1c). NaOH (1M) (t=5 min, A=−0.0686), (t=53 min, A=0.0048), (t=113 min, A=0.0293), (t=185 min, A=0.0370), (t=241 min, A=0.0837), (t=306 min, A=0.2096) (FIG. 1d). Buffer (pH=7.4) (t=5 min, A=−0.0067), (t=41 min, A=−0.0067), (t=93 min, A=−0.0087), (t=186 min, A=0.0084), t=1626 min, A=0.1537) (FIG. 1e).

Data from example 1 highlighted, the design of a delivery system suitable for interaction with TMPP, via ionic bond formation. The release profile showed the ability of the drug to dissociate from the delivery platform.

EXAMPLE 2

F$_T$([LYS][PTMO]):Ceramide

2a: Synthesis of Polymer F$_T$([LYS][PTMO])

Polytetramethyleneoxide (10 g, 0.0097 mol, predried) was dissolved in DMAc (50 mL). Lysine diisocyanate (4.11 g, 0.0194 mol, freshly distilled) in DMAc (25 mL) was added drop-wise to the polytetramethyleneoxide solution. The pre-polymer reaction mixture was sealed and maintained under a nitrogen atmosphere between 60-70° C. for two hours. The end capping agent, fluoro oligomer (11.74 g, 0.0194 mol) was dissolved in DMAc (25 mL) and added drop wise to the pre-polymer reaction mixture. The reaction solution was sealed under N$_2$ and stirred overnight at room temperature. Dibutyltin dilaurate was used as the catalyst. The product was precipitated in a mixture of water and ether for the recovery of the catalyst and removal of residual fluoro oligomer. The final product was dried under vacuum. NMR and IR analysis confirmed the presence of methyl ester groups. The ester functional groups were used for a number of reactions. For certain chemical reactions specific functional groups such as carboxylic acid groups were required. The hydrolysis of the ester groups to carboxylic acid groups was completed using (1.0 M), hydrochloric acid solution. The final product was precipitated in (1.0 M), aqueous KCl, washed and dried under vacuum at 60° C. The conversion of ester groups to acid functional groups was further confirmed by NMR analysis. Proton NMR indicated the disappearance of methoxy groups. The XPS analysis area was 700×300 microns in size with the following atomic content, C(38.6%), N(3.2%), O(10.2%), with a total fluorine content of (47.6%), by weight. IR analysis was in accordance with the chemical structure 3327.29 (cm$^{-1}$), ν(N—H), H-bonded, 2945.10 (cm$^{-1}$), ν(C—H), CH2 asymmetric stretching, 2865.69 (cm$^{-1}$), ν(C—H), CH2 symmetric stretching, 1717.91 (cm$^{-1}$), ν(C=O), urethane amide, 1533.54 (cm$^{-1}$), ν(C—N), stretching mode, 1445.56 (cm-1), ν(C—N), stretching mode, 1349.31 (cm$^{-1}$), ν(C—O), stretching, 1400-1000 ν(C—F), monofluoroalkanes absorb to the right in the range, while polyfluoroalkanes give multiple strong bands over the range from 1350-1100 (cm$^{-1}$). Elemental analysis $C_{92}H_{148}O_{25}N_4F_{30}$ was in accordance with the expected structure [% C, 48.56% (50.34% (−1.76%)), % H, 6.87% (7.07% (−0.2%)), % N, 2.53% (2.7% (−0.17%)), % F, 22.78% (20.37% (2.41%))]. $^1$H NMR spectrum (CDCl$_3$): δ$_H$ (300 MHz), 4.37 (15, 16, 17), 4.09 (1, 18), 3.75 (2), 3.42 (11), 3.17 (6), 2.46 (12), 1.63 (3, 4, 5, 9, 10), (FIG. 2).

2b: Complex Formation, Isolation and Dissociation Profile—C6-Ceramide 2a (0.1 g(acid)) was dissolved in dichloromethane (3 mL) at room temperature under an atmosphere of nitrogen. A model compound from sphingosine derivatives (Ceramide (C2:0), (C4:0), (C6:0), (C8:0), (C10:0), (C12:0), (C14:0), (C16:0), (C17:0), (C18:0), (C18:1), (C20:0), (C24:0), (C24:1)) (0.1 g) was dissolved in dichloromethane (3 mL). When completely in solution this mixture was added drop-wise, over 15 minutes, to the oligofluoro (2a) in solution. The reaction mixture was sealed and left under N$_2$ for two hours. The excess solvent was removed under pressure to allow the formation of the final product. The release/dissociation of the sphingosine compound (ceramide family) was confirmed using HPLC (0.5 mg/mL, injected 6 times, retention time 14.062 minutes) (FIG. 2l). This reaction procedure was further analyzed by polarized light microscopy and scanning electron microscopy. The polarized light microscopy results indicated that when the two components were simply mixed together and left at room temperature to allow the solvent to evaporate, a heterogenous matrix was formed (FIGS. 2a, 2b, 2c and 2d). This was further confirmed by scanning electron microscopy (FIGS. 2e, 2f, 2g and 2h). The homogeneity of the sample was further examined by using stainless steel unpolished metallic platforms. These platforms were coated with the product as a thin layer and then examined using scanning electron microscopy (FIGS. 2i and 2j). The results were indicative of a homogenous coating. Furthermore, the reaction procedure was analyzed to confirm that during the reaction and isolation of the final product the overall structure of the active compound was unaltered. Differential scanning electron microscopy (FIG. 2k) and NMR analysis confirmed the primary structure of the active compound remained intact. This composition was used to coat prototype devices which relates to endo-vascular devices. No phase separation was observed using Scanning Electron Microscopy (SEM) (FIGS. 2n, 2m, 2o and 2p).

The data from example 2, high-lighted the design of a delivery system suitable for interaction with C6-Ceramide, via hydrogen bonding. The release profile showed the ability of the drug to dissociate from the delivery platform. The homogeneity of the final product is further demonstrated by coating a spring as a product prototype.

EXAMPLE 3

$F_T$([LYS(Cyd)][PTMO]):Methyl Violet 2B

3a: Synthesis of Polymer [$F_T$[LYS(Cyd)][PTMO])]

Cyclodextrins (CyD) are cyclic, water-soluble, non-reducing compounds built from six, seven or eight sugar units. They possess hydrophobic cavities and capable of interacting with a great variety of molecular species. Geometrical rather than chemical factors are decisive in determining the suitability of the guest compound. The lysine based oligofluoro (OF) drug delivery matrix backbone (2a) was used as a platform for interacting with cyclodextrin, crown ethers and/or calixerenes.

6-Monodeoxy-6-monoamino-β-cyclodextrin.HCl salt (0.174 g) was dissolved in MilliQ water (0.5 mL). To de-salt, 1.0 N NaOH (50 uL) was added to neutralize the HCl and precipitate the 6-monodeoxy-6-monoamino-β-cyclodextrin (CyD) as a free base. The CyD was centrifuged at 1000 rpm for 10 minutes and the supernatant was removed. The free base 6-Monodeoxy-6-monoamino-β-cyclodextrin was purified and dried under vacuum. The oligofluoro (OF) (2a—(acid)) (0.105 g) was dissolved in anhydrous DMF (2 mL) and cooled to 0° C. DIC (21 µL) for 2 hours and the reaction mixture was stirred for 2 hours. CyD (56 mg) was dissolved in DMF (2 mL) and added dropwise to the activated OF with TEA (6 µl). The reaction mixture was sealed and kept under nitrogen for 7 days. The product CyD-OF (0.128 mg) was recovered from the DMF solvent by precipitation in water (5 mL). The final product was purified and dried in a 50° C. oven for 2 days. $^1$H NMR spectrum CyD-OF (DMSO): $\delta_H$ (300 MHz), 8.05 (NH-amide), 5.73 (H(C1-CyD)), 3.57 (H(C2, C3-CyD), 2.71 (H(C6')), (FIG. 3).

3b: Complex Formation, Isolation, and Release Profile—Methyl Violet

CyD-OF (3a) (2.7 g) was dissolved in DMSO (75 µL). A solution of Methyl Violet (MV, 2.8 mg) in DMSO (28 mL) was prepared at 0.1 mg/mL. One mL of Methyl Violet solution was further diluted with DMSO (10 mL) to form a 0.01 mg/mL solution. The CyD-OF solution (75 µL) was added dropwise to a solution of MV (500 µL) in a 4 mL glass vial over the course of ten minutes. This solution was sealed and left in the dark for 12 hours. A UV/Vis measurement of the Methyl Violet solution at 0.01 mg/mL was taken (A (591 nm)=0.96) as control. The UV/Vis spectrum of the CyD-OF was measured at A (591 nm)=0.63, indicating the intensity of the guest molecules evidently to change upon the addition of molecular receptors. Upon complexation the absorbance decreased, confirming the formation of a complex. A control solution was also prepared. This control solution had a mixture of OF, CyD and Methyl Violet at the same molar ratio as used for UV/Vis study anaylsis. The UV/Vis measurement of the Methyl Violet solution at 0.01 mg/mL was identical to the UV/Vis spectrum of the OF, CyD and Methyl Violet (i.e. no reduction in absorbance was noted).

Data from Example 3, high-lighted the design of a delivery system suitable for Endo/Exo mode of complexation. The UV absorption decrease indicated the Cyd complexation.

EXAMPLE 4

$F_T$([LYS(COO—Na+)][PTMO]):Cisplatin

4a: Synthesis of Polymer $F_T$([LYS(COO$^-$Na$^+$)][PTMO])

4a-1: A 10% solution of sodium carbonate equivalent to 2.5 excess of (2a-Ester) at (0.5 gram) was prepared. A solution of OF (2a) in methanol was slowly added into the sodium carbonate solution at room temperature. This reaction mixture was sealed under nitrogen and left stirring at room temperature for 72 hours. The end product was purified and dried under vacuum. NMR analysis was in accordance with the modified structure.

4a-2: A solution of OF (2a) with ester functional groups (2.024 g) was dissolved in methanol (20 mL). A solution of NaOH (1.0 N, 2.3 mL) was added dropwise to the OF (2a). This reaction mixture was left stirring under nitrogen for six hours. Excess solvent was removed under vacuum and the end product was purified and dried at 50° C. NMR analysis was in accordance with the modified structure ($^1$H NMR spectrum (CDCl$_3$): $\delta_H$ (300 MHz) (—OCH3 (3.74) eliminated).

4b: Complex Formation, Isolation, and Release Profile—Cis-Diamminedichloro Palatinate (II)

4b-1: (2a) (0.3 g) was dissolved in DMF (8 mL). Cis-diamminedichloro platinate (II) (0.078 g) was dissolved in DMF (8 mL). After complete dissolution of the cisplatin, the oligofluoro (OF) (4a) was added drop wise under continuous stirring. The reaction mixture was left to react for 4-8 hours at ambient temperature being constantly monitored by thin layer chromatography. The excess cisplatin was removed by centrifuge using an appropriate filtration membrane. The chelated product was lyophilized and stored at −20° C. The release profile was monitored using UV analysis (FIG. 4b).

4b-2: (4a-2) (0.3 g) was dissolved in water (5 mL). Cis-diamminedichloro platinate (II) (0.078 g) was dissolved in water (20 mL). After complete dissolution of the cisplatin, the oligofluoro (OF) (4a) was added drop wise under continuous stirring. The reaction was left to react for 4-8 hours at ambient temperature being constantly monitored by thin layer chromatography. The excess cisplatin was removed by centrifuge using an appropriate filtration membrane. The chelated product was lyophilized and stored at −20° C. Elemental analysis indicated a total platin content of 11.1%. The release profile was registered using UV analysis (FIG. 4b).

Data from example 4, high-lighted the design of a delivery system suitable for interaction with cisplatin, via chelation. The release profile showed the ability of the drug to dissociate from the delivery platform. The total platin content indicated a suitable drug loading.

EXAMPLE 5

$F_T([LYS(PEG)][PTMO])$:Methotrexate(MTX)

5a: Synthesis of Polymer $F_T([LYS(Ethanolamine)][PTMO])$

The lysine based OF (2a) was used as a platform for covalent attachment of ethanolamine. This chemical modification was achieved via amide formation. OF (2a) (1.042 g) was dissolved in anhydrous MeOH (35 mL). Potassium carbonate (245 mg) was added to the solution and vigorously stirred to obtain a clear solution. Ethanolamine (108 mg) was added to the reaction mixture, under a nitrogen atmosphere. This reaction mixture was gently refluxed for seven days. The final product was purified and dried in a 50° C. oven for 2 days. NMR result was consistent with the proposed structure.

5b: Synthesis of Polymer $F_T([LYS(PEG)][PTMO])$

OF (5a) (0.105 g) was dissolved in DMF (2 mL). To this solution was added TEA (19 mL) (solution A). FMOc-PEG-NHS (460 mg) in DMF (5 mL) was transferred to a 2-neck reaction flask (solution B). Solution A was added to solution B, dropwise under a nitrogen atmosphere. The reaction mixture was sealed and left under nitrogen for 12 hours. The FMOc protected product was purified and dried in a 40° C. oven. For deprotection step a 20% piperidine solution was used. The final product was purified and dried in a 40° C. oven. NMR result was consistent with the proposed structure.

5c: Complex Formation, Isolation, and Dissociation Profile—Methotrexate

The PEG-OF (5b) (0.003 g) was dissolved in DMSO (2 mL). This solution was added dropwise (30 minutes) to a solution of freshly prepared methotrexate (0.3 mg) in DMSO (1 mL). This reaction mixture was allowed to stir for 24 hours under nitrogen. The final product was isolated, purified and dried under vacuum. To illustrate the dissociation profile of the MTX an ultraviolet analysis was performed at (1=371 nm), (t=30 min, A=0.859); (t=60 min, A=0.900), (t=120 min, A=0.942).

5d: Complex Formation, Isolation, and Dissociation Profile as an Example of Salt Formation—$F_T([LYS][PTMO])$:Chlorhexidine OF (2a) was used as a platform for the delivery of chlorhexidine (CHX) (5d-c). The OF (2a) (0.3 g) was dissolved in DMAc (3 mL). A solution of CHX (263 mg) in DMAc (3 mL) was added dropwise to the solution of OF over 2 hours. The reaction mixture was sealed and left under nitrogen for 24 hours. The final product was isolated, purified and dried under vacuum for 24 hours.

Film preparation: The isolated product (OF:CHX) was combined with a 10% solution of Carbothane 85A in DMF as a solid (52 mg) (50-130) (5d-e) or pre-solvated at the same concentration (50-140) (5d-f). Each of these solutions (6 mL), were transferred into 4 cm×4 cm PTFE wells and cast into films.

A series of control films were similarly prepared, according to the experimental details, with these solutions: 10% Carbothane 85A (50-100) (5d-a); CHX (26 mg) was added to 6 mL of the 85A solution (50-110) (5d-b); OF (2a) (33 mg) was added to 6 mL of the 85A solution (50-120) (5d-c).

XPS results indicated surface activity in the first 10 nm through fluorine percentages. The presence of CHX was confirmed based on chlorine percentages (FIG. 5d-g). SEM images of all films are shown in FIGS. (5d-a, 5d-b, 5d-c, 5d-e and 5d-f). CHX in Carbothane showed crystallization of the drug at the surface and lack of a homogenous platform (5d-b). SEM images of (Carbothane 85A(OF:CHX)) showed a homogenous platform with no phase separation.

Release profile: Strips of films (4 cm×0.5 cm) were cut and further divided into 0.5×0.5 cm segments, keeping the overall concentration the same between all samples. These samples were placed in glass vials containing water (1.5 mL). UV/Vis absorbance was measured at various timepoints (1, 2, 3, 4, 96 hours) (5d-h). This data showed the differences in CHX release as well as the ability of the drug delivery platform to allow release.

Data from example 5, high-lighted the design of a delivery system suitable for interaction with CHX, via acid salt formation. The release profile showed the ability of the drug to dissociate from the delivery platform. The homogeneity of the final product was further demonstrated by SEM.

EXAMPLE 6

$F_T([LDI][PTMO])$:Ibuprofen

6a: Synthesis of Polymer $F_T([LDI](PFB)[PTMO])$

Lysine based OF (2a) was used as a platform for covalent attachment of a fluorinated phenyl group. OF (2a) (0.496 g) was added into a 2-neck flask (100 ml) containing anhydrous DMF (5 ml). DIC (100 µL) was added and the reaction mixture was sealed and left stirring under nitrogen for 20 minutes (solution A).

Perfluorobenzyl alcohol (PFBA) (128 mg) was dissolved in DMF (5 ml). After complete dissolution, TEA (90 µL) was added (solution B). Solution B was added dropwise to solution A. This reaction mixture was sealed and left stirring under nitrogen for 12 hours. The PFBA-OF was recovered from solvent and dried. This product was further washed with 1-octanol (3×3 mL) to extract excess PFBA. The final product was purified and dried under vacuum for 24 hours. $^1$H NMR spectrum (CDCl$_3$): $\delta_H$ (300 MHz), 5.30 (19), 4.33-4.38 (15, 16, 17), 4.04-4.09 (1, 18), 3.74 (2), 3.39-3.43 (11), 3.17 (6), 2.46 (12), 1.63 (3, 4, 5, 9, 10), (FIG. 6a).

6b: Synthesis of Polymer $F_T(PFB)([LDI][PTMO])$

PTMO (5.002 g) was weighed into a dry 2-neck flask and degassed for 2 hours. PFBA (2.002 g) was weighed into another 2-neck flask and degassed for 2 hours. Anhydrous DMAc (15 mL) was added to each flask, keeping everything under a continuous flow of nitrogen. LDI (1.964 g) was dissolved in DMAc (15 mL) and mixed with 333 mg of dibutyltin dilaurate catalyst. This solution was added dropwise to the PTMO solution, using a syringe. This reaction was maintained at 70° C. for 2 hours under a nitrogen atmosphere (solution A). After 2 hours, PFBA solution was added to solution A dropwise, and the reaction mixture was maintained at room temperature for 24 hours. It is essential to eliminate water from this polymerization reaction. The product was recovered, precipitated and purified to remove unreacted starting materials. The final product was dried at 50° C. oven for two days. $^1$H NMR spectrum (CDCl$_3$): $\delta_H$ (300 MHz), 5.30 (20), 4.40 (15, 16, 17), 4.06-4.08 (1, 18), 3.74 (2), 3.35-3.41 (11), 3.14-3.19 (6), 1.37-1.70 (3, 4, 5, 9, 10), (FIG. 6b).

Figure 6H:
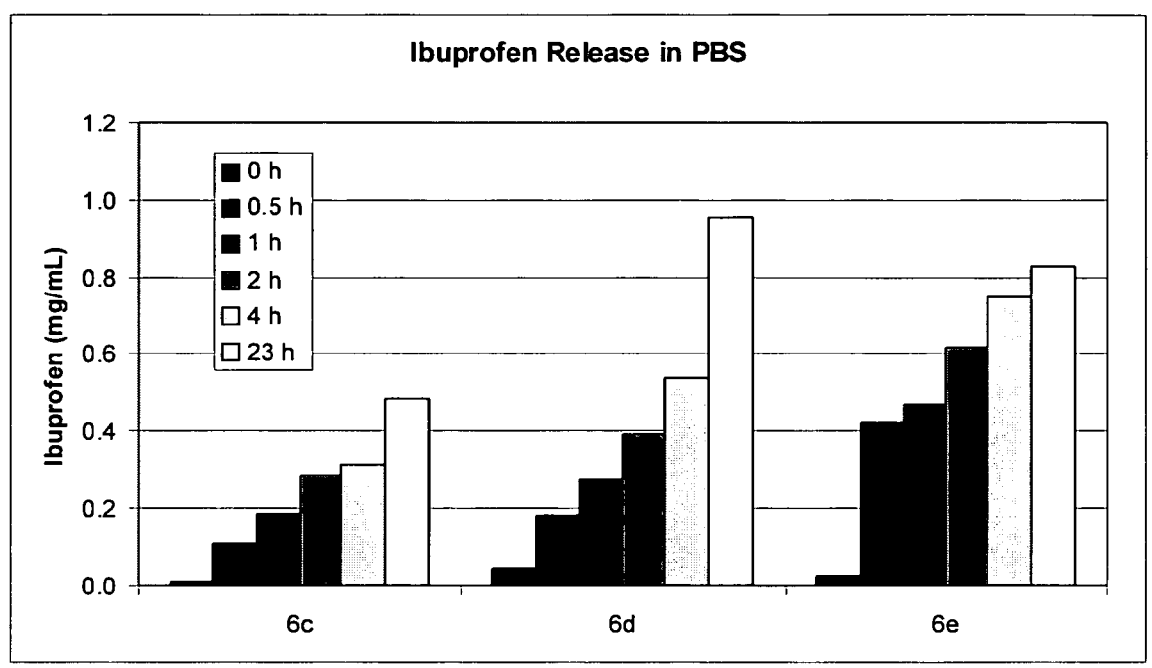
Figure 7A:
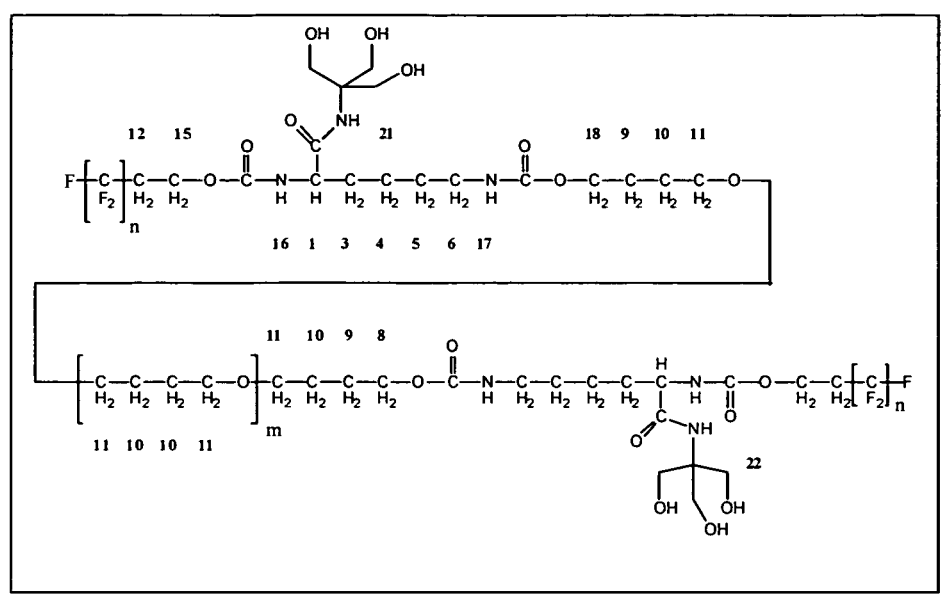

6c: Complex Formation, Isolation and Release Profile—Ibuprofen $F_T([LDI](PFB)[PTMO](6a)$:Ibuprofen OF (6a) (0.050 g) was dissolved in chloroform (1 mL) at room temperature under nitrogen. Ibuprofen (0.009 g) was dissolved in chloroform (0.5 mL). When completely dissolved this mixture was added dropwise, over 30 minutes, to the OF solution (6a). The reaction mixture was sealed and left under N$_2$ for four hours. The excess solvent was removed and the final product was isolated, purified and dried. The release profile was monitored using UV analysis (FIG. 6h).

6d: Complex Formation, Isolation and Release Profile—Ibuprofen
$F_T(PFB)([LDI][PTMO])$:Ibuprofen OF (6b) (0.5 g) was dissolved in chloroform (5 mL) at room temperature under nitrogen. Ibuprofen (0.109 g) was dissolved in chloroform (1.5 mL). When completely dissolved this mixture was added dropwise, over 60 minutes, to the OF solution (6b). The reaction mixture was sealed and left under N2 for four hours. The excess solvent was removed and the final product was isolated, purified and dried. The release profile was monitored using UV analysis (FIG. 6h).

6e: Complex Formation, Isolation and Release Profile—Ibuprofen
$F_T([LDI][PTMO])$:Ibuprofen OF (2a) (0.3 g) was dissolved in chloroform (5 mL) at room temperature under nitrogen. Ibuprofen (0.053 g) was dissolved in chloroform (1.0 mL). When completely dissolved this mixture was added dropwise, over 45 minutes, to the OF solution (2a). The reaction mixture was sealed and left under N2 for four hours. The excess solvent was removed and the final product was isolated, purified and dried. The release profile was monitored using UV analysis (FIG. 6h).

Film preparation: The isolated products (6c, 6d, 6e) (10 mg each) were dissolved in DMF (0.5 mL), and the solutions (375 mL each) were combined with a 10% DMF solution of Chronothane 80A (1.5 mL). Each solution of Chronothane+OF (179 mL each) was pipetted into 6 mm polypropylene flat bottom wells and cast into films.

A series of control films were cast, to study the surface activity of 6a and 6b. 6a and 6b (10 mg each) were dissolved in DMF (0.5 mL), and 25 uL of these solutions were combined with polycarbonate polyurethane (PCNU). The solutions (150 mL each) were pipetted into 6 mm polypropylene flat bottom wells and cast into films. XPS analysis of the PCNU films indicated the surface activity in the first 10 nm through fluorine percentages (FIG. 6h).

Data from example 6, high-lighted the design of a delivery system suitable for interaction with Ibuprofen, via p-p stacking. The release profile showed the ability of the drug to dissociate from the delivery platform. The XPS data results indicated the presence of flourine in the top 10 nm of the surface (see Table 1).

TABLE 1

| Films | C % | N % | O % | F % | Sn % |
| --- | --- | --- | --- | --- | --- |
| PCNU | 80.2 | 1.8 | 14.7 | 2.7 | 0.1 |
| PCNU + 0.5 wt % 6a | 50.3 | 3.5 | 14.0 | 32.0 | 0.2 |
| PCNU + 0.5 wt % 6b | 63.6 | 2.6 | 23.6 | 8.6 | 0.9 |

EXAMPLE 7

$F_T([LYS(Tris)][PTMO])$

Synthesis of Polymer $F_T([LYS(Tris)][PTMO])$

OF 2a (0.997 g) was transferred into an oven dried two-neck flask (100 mL) and degassed for 2 hours. Anhydrous methanol (33 mL) was added and the reaction mixture was stirred until everything was in solution. A mixture of trihydroxymethyl aminoethane (Tris) (205.8 mg) and anhydrous potassium carbonate (234.8 mg) was added. This reaction mixture was refluxed at 45° C. for seven days. The final product was purified and dried under vacuum for 48 hours (30° C.). $^1$H NMR spectrum (CDCl$_3$): $\delta_H$ (300 MHz), 4.37 (15, 16, 17), 4.05 (1, 18), 3.75 (2), 3.62-3.69 (22), 3.40-3.43 (11), 3.17 (6), 2.46 (12), 1.61-1.66 (3, 4, 5, 9, 10).

This example highlighted the design of a polyvalent platform.

EXAMPLE 8

Polycaprolactone (PCL)[OF:Salicylic Acid]

When a biologically active agent is included within a polymeric lattice with crystalline properties, for example, polypropylene, polytetrafluoroethylene, nylon, poly(ethylene therephthalate) or polycaprolactone, the release profile is generally based on one time dissociation or incomplete dissociation. In many cases this is due to structural properties of the crystalline platform.

For this example initially, the compatibility between the crystalline matrix, polycaprolactone (PCL) and oligofluoro (OF) was established.

8a: OF (2a-acid) (0.208 g) was dissolved in dichloromethane (3 mL). Salicylic acid (0.072 g) was dissolved in dichloromethane (3 mL). The salicylic acid solution was added to the OF solution dropwise over 45 minutes. The reaction mixture was sealed and left under nitrogen for 24 hours. The final product was purified and dried under vacuum for 48 hours.

8b: OF $F_T([MDI][PTMO])$ (0.208 g) was dissolved in dichloromethane (3 mL). Salicylic acid (0.072 g) was dissolved in dichloromethane (3 mL). The salicylic acid solution was added to the OF solution dropwise over 45 minutes. The reaction mixture was sealed and left under nitrogen for 24 hours. The final product was purified and dried under vacuum for 48 hours.

Film preparation: Polycaprolactone(8a): 8a (50 mg) was added to a 10% solution of PCL in DCM (10 mL). This solution (5 mL) was transferred into 4×4 cm PTFE wells and cast into films. Polycaprolactone(8b): 8b (50 mg) was dissolved in DMF (0.5 mL). This solution was added to a 10% solution of PCL. This solution (5 mL) was transferred into 4 cm×4 cm PTFE wells and cast into films.

A series of control films were similarly prepared, according to the experimental details, with these solutions: 10% PCL; SA (0.009 g) was added to 10% PCL (10 mL). 5% OF; OF (0.05 g) was added to 10% PCL (10 mL).

Figure 8C:
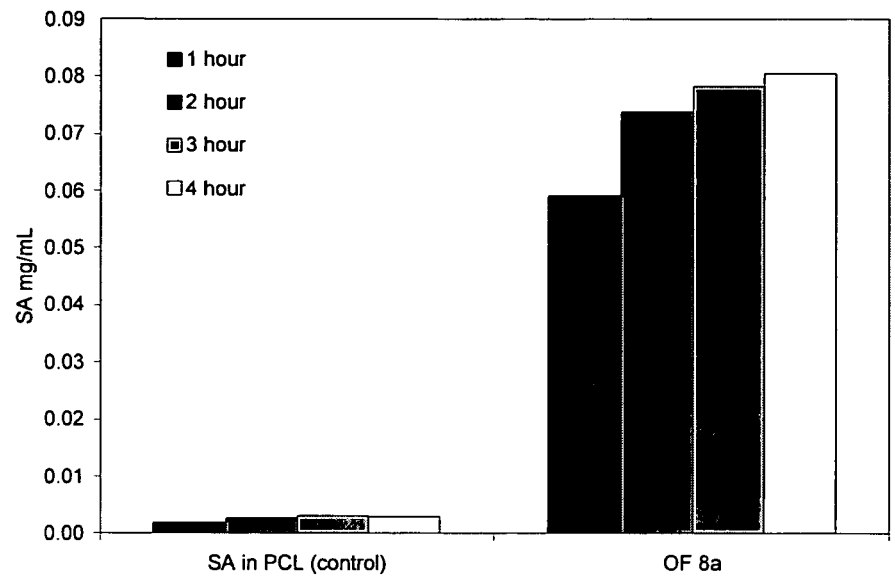
Figure 8D:
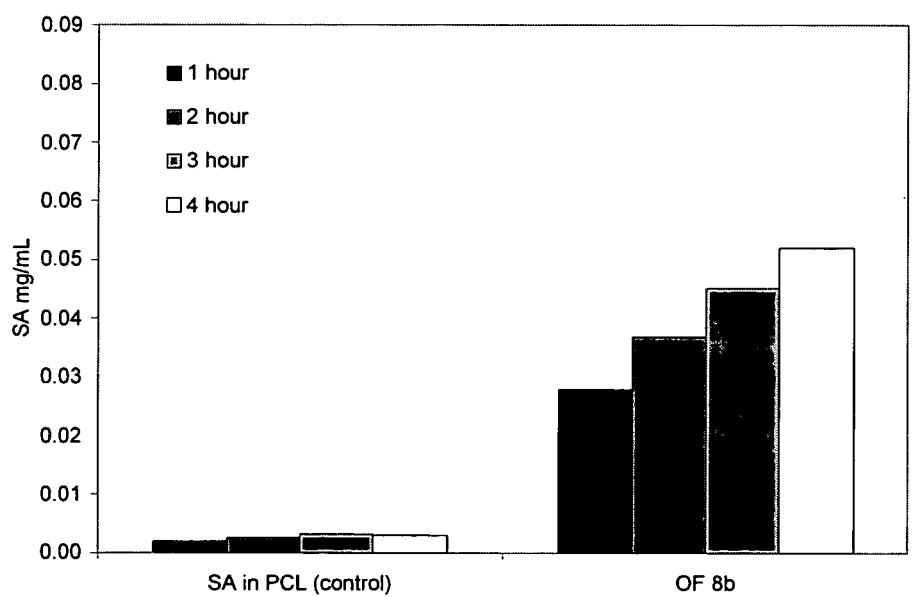

Release profile: Strips of films (4×0.5 cm) were cut and further divided into (0.5×0.5 cm) segments, keeping the overall concentration the same between all samples. These samples were placed in glass vials containing PBS (1.5 mL). UV/Vis absorbance was measured at various timepoints (1, 2, 3 and 4 hours) (FIG. 8c and FIG. 8d).

Data from example 8, high-lighted the design of a delivery system suitable for interaction with Salicylic acid and compatible with the base polymer to form a homogenous matrix. The release profile indicated the ability of the drug to be released from the base polymer in the presence of delivery platform.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A polymer described by the formula:

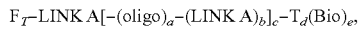

wherein $F_T$ is a polyfluoroorgano group;

Bio is one or more biologically active agents capable of being complexed to LINK A;

each LINK A is, independently, an organic moiety comprising a complexing moiety that is tri-hydroxymethyl aminoethane (Tris);

oligo is an oligomeric segment;

T is a terminal group;

a is 0 or 1;

b, c, d, and e are integers greater than 0; and wherein at least one Bio is complexed via hydrogen bonding interactions to at least one LINK A, and wherein each Bio is selected from the group consisting of antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, psychoactive drugs, vitamins, lipids, and prodrugs thereof.

2. The polymer of claim 1, wherein $F_T$ is a polyfluoroalkyl.

3. The polymer of claim 1, wherein $F_T$ has a molecular weight of between 100-1,500 Da.

4. The polymer of claim 1, wherein $F_T$ is selected from the group consisting of radicals of the general formula $CF_3(CF_2)_r CH_2CH_2$— wherein r is 2-20, and $CF_3(CF_2)_s(CH_2CH_2O)_\chi$ wherein $\chi$ is 1-10 and s is 1-20.

5. The polymer of claim 1, wherein said Oligo is a branched or non-branched oligomeric segment with 20 or more repeating units.

6. The polymer of claim 1, wherein said LINK A is a monomeric segment.

7. The polymer of claim 1, wherein a is 0.

8. The polymer of claim 1, wherein said oligomeric segment comprises polyurethane, polyurea, polyamides, polyalkylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, polytetramethyleneoxide, or polyethylenebutylene segments.

9. The polymer of claim 1, wherein said oligomeric segment has an absolute molecular weight of greater than about 10 kDa.

10. The polymer of claim 1, wherein said polyfluoroorgano group comprises from about 0.01 to 5 weight % of said polymer.

11. The polymer of claim 1, wherein said oligomeric segment has an absolute molecular weight of less than about 10 kDa.

12. An admixture comprising a polymer of claim 1 admixed with a base polymer.

13. The admixture of claim 12, wherein said base polymer is selected from polyurethanes, polysulfones, polycarbonates, polysaccharide, polyesters, polyethylene, polypropylene, polystyrene, poly(acrylonitrile-butadienestyrene), polybutadiene, polyisoprene, styrenebutadiene-styrene block copolymers, styrene-iso-prenestyrene block copolymers, poly-R-methylpentene, polyisobutylene, polymethyl-methacrylate, polyvinylacetate-polyacrylonitrile, polyvinyl chloride, polyethylene terephthalate, cellulose and its esters, polyamides, polyester-polyethers, styrene-isoprenes, styrene butadienes, thermoplastic polyolefins, styrene-saturated olefins, polyester-polyester, ethylene-vinyl acetate ethylene-ethyl acrylate, ionomers, thermoplastic polydienes, and combinations thereof.

14. A shaped article formed from a polymer of claim 1.

15. A shaped article formed from an admixture of claim 12.

16. The shaped article of claim 14 or 15, wherein said article is an implantable medical device.

17. The shaped article of claim 14 or 15, wherein said article is a cardiac-assist device, a catheter, a stent, a prosthetic implant, an artificial sphincter, or a drug delivery device.

18. The shaped article of claim 14 or 15, wherein 80% of the biologically active agent is released within 2 years.

19. The shaped article of claim 18, wherein $t_{10}$ is greater than 1/10 of $t_{50}$.

20. A composition for the controlled release of a biologically active agent comprising a polymer of claim 1, wherein said composition is formulated as a cream, gel, or lotion.

21. A composition for controlling the proliferation of pests comprising a polymer of claim 1, wherein said biologically active agent is an pesticide or herbicide.

22. A composition for reducing microbial growth on a surface comprising a polymer of claim 1, wherein said biologically active agent is an antimicrobial agent.

23. A shaped article comprising a polymer of claim 1.

24. The shaped article of claim 23, wherein said article is coated with said polymer.

* * * * *